US010908136B2

(12) United States Patent
Sim et al.

(10) Patent No.: US 10,908,136 B2
(45) Date of Patent: Feb. 2, 2021

(54) ELECTRONIC DEVICE HAVING STRUCTURE WITH GAS SENSOR

(71) Applicant: Samsung Electronics Co., Ltd., Gyeonggi-do (KR)

(72) Inventors: Bokyung Sim, Gyeonggi-do (KR); Seunggoo Kang, Gyeonggi-do (KR); Jeonggyu Jo, Gyeonggi-do (KR); Dongil Son, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 121 days.

(21) Appl. No.: 16/208,750

(22) Filed: Dec. 4, 2018

(65) Prior Publication Data
US 2019/0170716 A1 Jun. 6, 2019

(30) Foreign Application Priority Data
Dec. 5, 2017 (KR) ........................ 10-2017-0166204

(51) Int. Cl.
*G01N 33/00* (2006.01)
*F24F 11/57* (2018.01)
(Continued)

(52) U.S. Cl.
CPC ........... *G01N 33/0031* (2013.01); *F24F 3/16* (2013.01); *F24F 11/57* (2018.01); *G01N 1/22* (2013.01);
(Continued)

(58) Field of Classification Search
CPC .. G01N 33/0031; G01N 33/0073; G01N 1/22; G01N 33/0042; G01N 33/0047;
(Continued)

(56) References Cited

U.S. PATENT DOCUMENTS

| 2014/0193018 A1 | 7/2014 | Lim et al. |
| 2015/0182146 A1 | 7/2015 | Hidaka |

(Continued)

FOREIGN PATENT DOCUMENTS

| CN | 206195854 U | 5/2017 |
| EP | 3 076 638 A1 | 10/2016 |

(Continued)

OTHER PUBLICATIONS

European Search Report dated Feb. 20, 2019.
International Search Report dated Mar. 11, 2019.
European Search Report dated dated May 14, 2019.

*Primary Examiner* — Robert R Raevis
(74) *Attorney, Agent, or Firm* — Cha & Reiter, LLC.

(57) ABSTRACT

An electronic device includes a housing having a hole formed therein, an audio device inside the housing and communicating with an outside of the electronic device through the hole, a gas sensor inside the housing and communicating with the outside through the hole, a proximity sensor inside the housing, a wireless communication module inside the housing, and a processor inside the housing. The processor is configured to acquire data associated with air outside the electronic device by using the gas sensor, to recognize a user gesture of starting a proximity call by using the proximity sensor, and to calculate air quality of the outside air based on at least one of data acquired by the gas sensor before the proximity call starting gesture is recognized and data acquired by the gas sensor after a gesture of ending the proximity call is recognized. Other various embodiments are possible.

16 Claims, 17 Drawing Sheets

(51) Int. Cl.
*F24F 3/16* (2021.01)
*G01N 1/22* (2006.01)
*H04M 1/02* (2006.01)
*H04M 1/03* (2006.01)
*F24F 110/50* (2018.01)

(52) U.S. Cl.
CPC ........ G01N 33/0073 (2013.01); H04M 1/026 (2013.01); H04M 1/03 (2013.01); *F24F 2110/50* (2018.01); *H04M 2250/12* (2013.01)

(58) Field of Classification Search
CPC ............... G01N 1/2205; G01N 1/2273; G01N 2001/2276; G01N 2001/2244; G01N 33/4972; G01N 33/98; F24F 11/57; F24F 3/16; F24F 2110/50; H04M 1/026; H04M 1/03; H04M 2250/12; A61B 5/0823; A61B 2010/0087; A61B 2010/0009
USPC ... 73/1.06, 23.3, 23.31, 23.34, 31.01, 31.02; 600/530; 340/632, 870.01, 870.02, 340/870.05
See application file for complete search history.

(56) References Cited

U.S. PATENT DOCUMENTS

| | | |
|---|---|---|
| 2015/0219608 A1 | 8/2015 | Choi et al. |
| 2015/0226585 A1 | 8/2015 | Yang |
| 2017/0130981 A1 | 5/2017 | Willette et al. |
| 2017/0191860 A1 | 7/2017 | Thuillier |
| 2017/0318135 A1 | 11/2017 | Han et al. |
| 2017/0318136 A1 | 11/2017 | Han et al. |
| 2018/0109658 A1 | 4/2018 | Le et al. |
| 2018/0367656 A1* | 12/2018 | Kim ........................ G06F 21/32 |

FOREIGN PATENT DOCUMENTS

| | | |
|---|---|---|
| EP | 3 187 865 A1 | 7/2017 |
| EP | 3 240 264 A1 | 11/2017 |
| EP | 3 240 272 A1 | 11/2017 |
| JP | 5316381 B2 | 7/2013 |

* cited by examiner

FIG. 4C
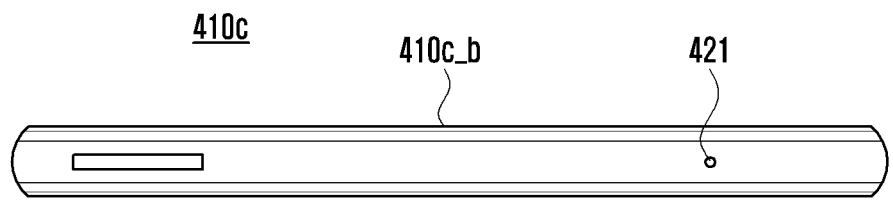
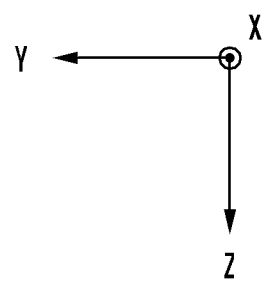

FIG. 6A
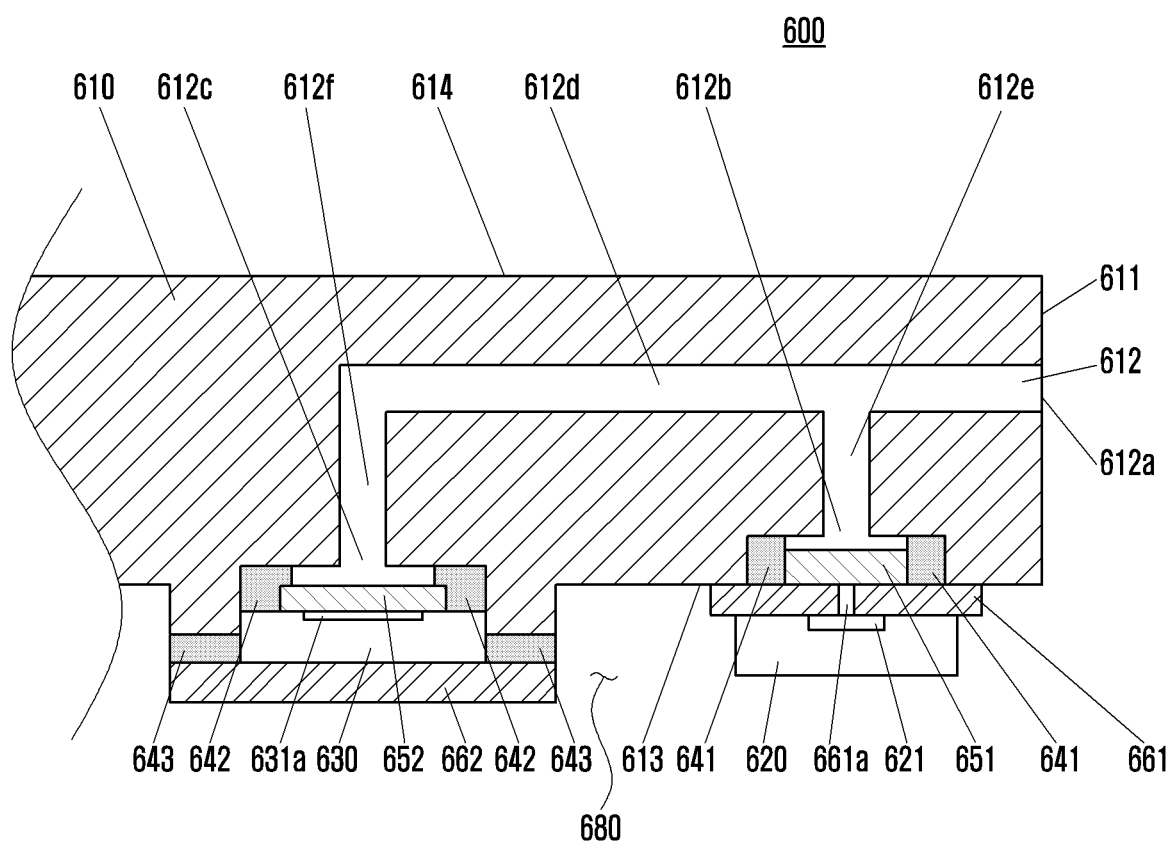
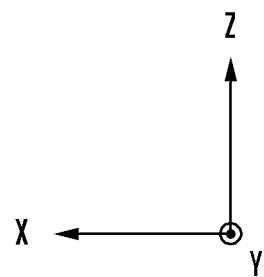

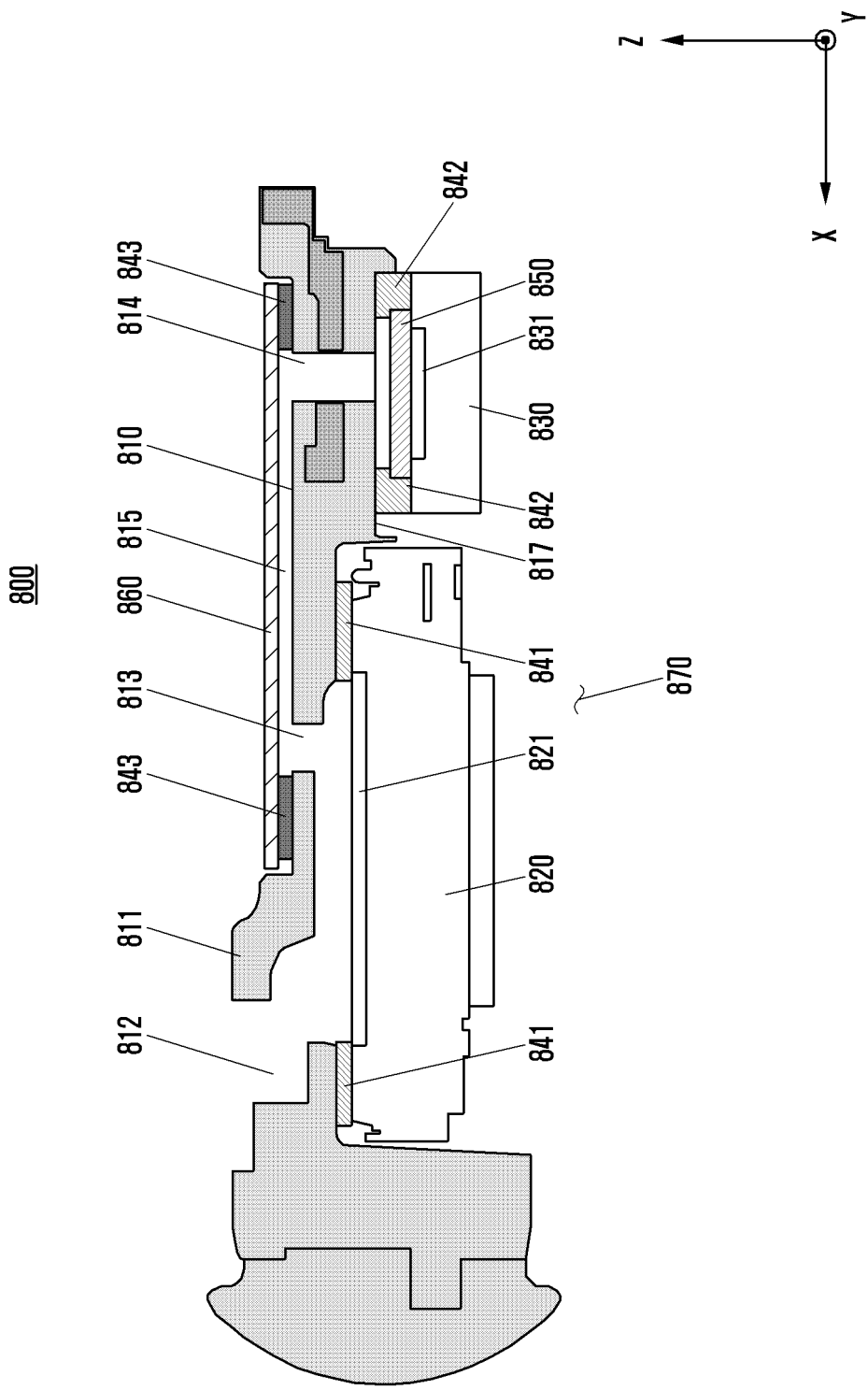

ic device in a network environment according to various embodi-
ELECTRONIC DEVICE HAVING STRUCTURE WITH GAS SENSOR

CROSS-REFERENCE TO RELATED APPLICATION

This application is based on and claims priority under 35 U.S.C. § 119 to Korean Patent Application No. 10-2017-0166204, filed on Dec. 5, 2017, in the Korean Intellectual Property Office, the disclosure of which is incorporated by reference herein in its entirety.

TECHNICAL FIELD

Embodiments of the present disclosure generally relate to an electronic device having a structure equipped with a gas sensor for analyzing the composition of an outside air.

BACKGROUND

Conventionally, the measurement of an air quality is performed at a specific place by a specialized agency, such as an environmental agency. As interest in air quality has increased recently, some mobile electronic devices (e.g., smart phones) having a gas sensor capable of measuring the air quality are being released.

SUMMARY

Equipping a gas sensor inside an electronic device requires a hole that can directly and fluidically communicate with the external environment of the electronic device. However, to improve, for example, the water resistant characteristics of electronic devices, adding holes to the external housing of the electronic devices has been disfavored.

Various embodiments of the present disclosure provide a structure in the electronic device in which a gas sensor shares a hole with other components such as a receiver or a microphone. This way, an advantage can be realized in that additional holes need not be added to the housing of the electronic device. In addition, one or more embodiments of the present disclosure provide an electronic device configured to perform a particular function based on information acquired via a gas sensor.

According to an embodiment of the present disclosure, an electronic device may comprise a housing having a hole formed therein; an audio device located inside the housing and communicating with an outside of the electronic device through the hole; a gas sensor located inside the housing and communicating with the outside through the hole; a proximity sensor located inside the housing; a wireless communication module located inside the housing; and a processor located inside the housing and electrically connected to the audio device, the gas sensor, the proximity sensor, and the wireless communication module. The processor may be configured to acquire data associated with air outside the electronic device by using the gas sensor, to recognize a user gesture of starting a proximity call by using the proximity sensor, and to calculate a quality of the outside air, based on at least one of data acquired by the gas sensor before the proximity call starting gesture is recognized, or data acquired by the gas sensor after a gesture of ending the proximity call is recognized.

According to an embodiment of the present disclosure, an electronic device may comprise a housing having a hole formed therein; a microphone located inside the housing and communicating with an outside of the electronic device through the hole; a gas sensor located inside the housing and communicating with the outside through the hole; a proximity sensor located inside the housing; a wireless communication module located inside the housing; and a processor located inside the housing and electrically connected to the microphone, the gas sensor, the proximity sensor, and the wireless communication module. The processor may be configured to recognize a user gesture of starting a proximity call, based on at least data acquired from the proximity sensor when the electronic device is in communication with an external device via the wireless communication module, and to measure a user's health status, based on at least data acquired by the gas sensor after the user gesture of starting the proximity call is recognized.

According to an embodiment of the present disclosure, a method for operating an electronic device may comprise acquiring, by a gas sensor of the electronic device, data associated with air outside the electronic device; recognizing, by a processor of the electronic device, a user gesture of starting a proximity call, based on at least data acquired from a proximity sensor of the electronic device when the electronic device is in communication with an external device via a wireless communication module of the electronic device; and calculating, by the processor, air quality based on at least one of data acquired by the gas sensor before the proximity call starting gesture is recognized and data acquired by the gas sensor after a gesture of ending the proximity call is recognized.

According to an embodiment of the present disclosure, a method for operating an electronic device may comprise recognizing, by a processor of the electronic device, a user gesture of starting a proximity call, based on at least data acquired from a proximity sensor of the electronic device when the electronic device is in communication with an external device via a wireless communication module of the electronic device; and measuring, by the processor, a user's health status, based on at least data acquired by a gas sensor of the electronic device after the user gesture of starting the proximity call is recognized.

According to an embodiment of the present disclosure, a mobile electronic device is capable of gas measurement through an existing hole being used for other purposes (e.g., sound output or sound acquisition) without requiring a separate hole dedicated to the gas sensor. Also, according to various embodiments of the present disclosure, an electronic device is configured to perform specific functions based on information acquired via the gas sensor.

Additional aspects will be set forth in part in the description which follows and, in part, will be apparent from the description, or may be learned by practice of the presented embodiments

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 4C is a plan view showing an upper side of the electronic device of FIG. 4A.

FIG. 6A is a cross-sectional view showing a structure equipped with a microphone and a gas sensor according to an embodiment.

FIG. 8 is a cross-sectional view showing a structure equipped with a receiver and a gas sensor according to an embodiment.

DETAILED DESCRIPTION

Figure 1:
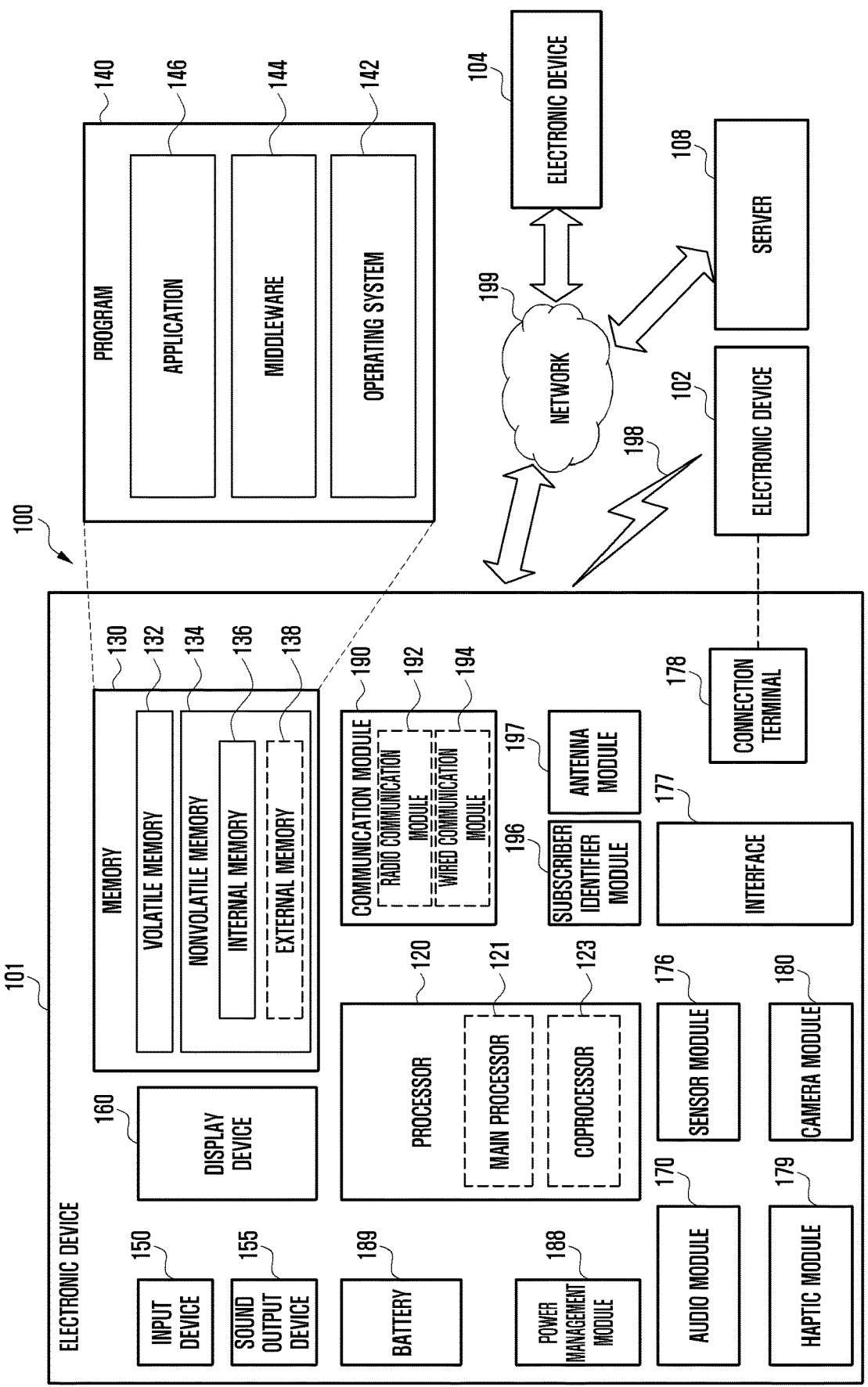
FIG. 1 is a block diagram illustrating an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may generate an electric signal or data value corresponding to an operational state (e.g., power or temperature) of the electronic device 101 or an environmental state external to the electronic device 101. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, a gas sensor (e.g., an electronic nose sensor), or an illuminance sensor. In some embodiments, two or more sensors (e.g., a temperature sensor, a humidity sensor, and a gas sensor) may be integrated into a single sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service.

The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
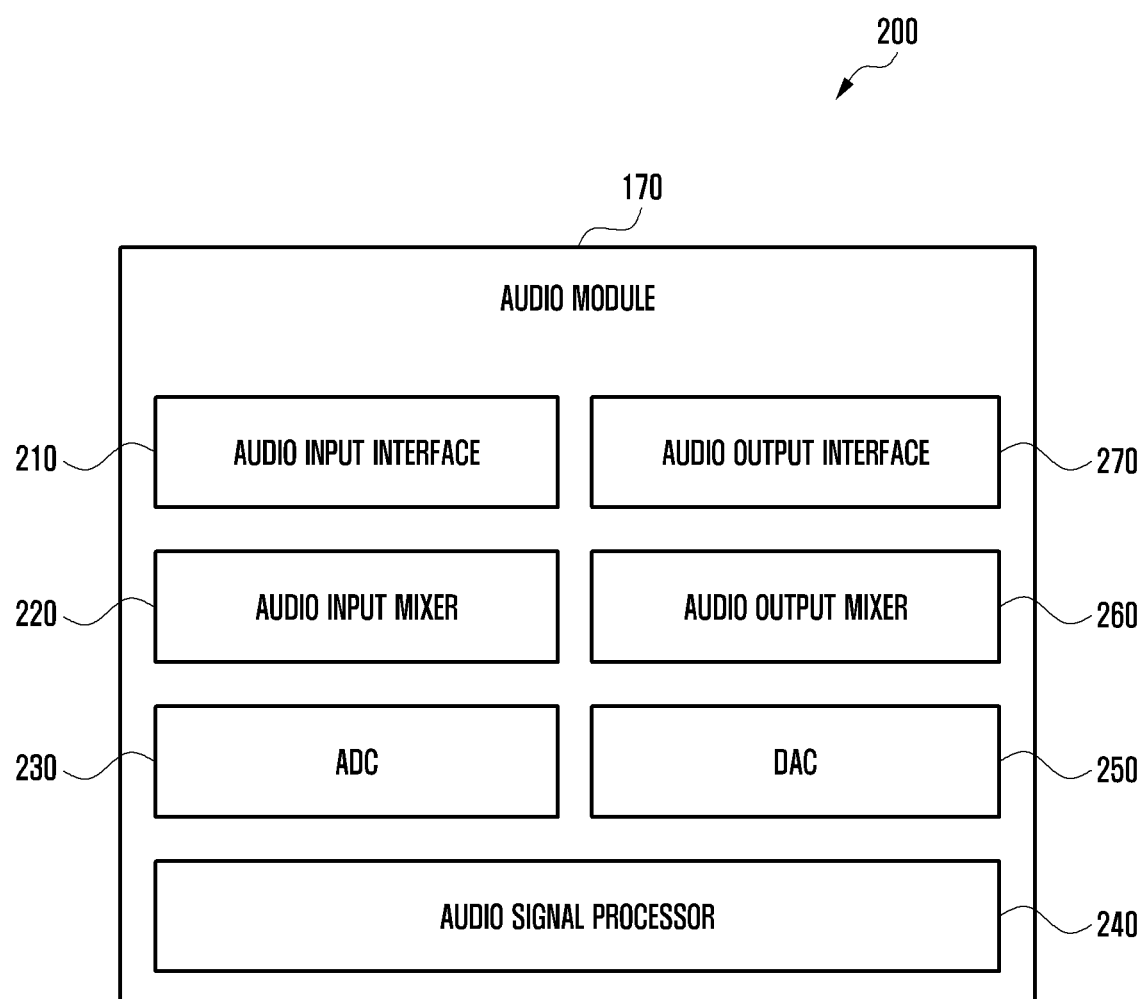
FIG. 2 is a block diagram illustrating an audio module according to various embodiments.

FIG. 2 is a block diagram 200 illustrating the audio module 170 according to various embodiments. Referring to FIG. 2, the audio module 170 may include, for example, an audio input interface 210, an audio input mixer 220, an analog-to-digital converter (ADC) 230, an audio signal processor 240, a digital-to-analog converter (DAC) 250, an audio output mixer 260, or an audio output interface 270.

The audio input interface 210 may receive an audio signal corresponding to a sound obtained from the outside of the electronic device 101 via a microphone (e.g., a dynamic microphone, a condenser microphone, or a piezo microphone) that is configured as part of the input device 150 or separately from the electronic device 101. For example, if an audio signal is obtained from the external electronic device 102 (e.g., a headset or a microphone), the audio input interface 210 may be connected with the external electronic device 102 directly via the connecting terminal 178, or wirelessly (e.g., Bluetooth™ communication) via the wireless communication module 192 to receive the audio signal. According to an embodiment, the audio input interface 210 may receive a control signal (e.g., a volume adjustment signal received via an input button) related to the audio signal obtained from the external electronic device 102. The audio input interface 210 may include a plurality of audio input channels and may receive a different audio signal via a corresponding one of the plurality of audio input channels, respectively. According to an embodiment, additionally or alternatively, the audio input interface 210 may receive an audio signal from another component (e.g., the processor 120 or the memory 130) of the electronic device 101.

The audio input mixer 220 may synthesize a plurality of inputted audio signals into at least one audio signal. For example, according to an embodiment, the audio input mixer 220 may synthesize a plurality of analog audio signals inputted via the audio input interface 210 into at least one analog audio signal.

The ADC 230 may convert an analog audio signal into a digital audio signal. For example, according to an embodiment, the ADC 230 may convert an analog audio signal received via the audio input interface 210 or, additionally or alternatively, an analog audio signal synthesized via the audio input mixer 220 into a digital audio signal.

The audio signal processor 240 may perform various processing on a digital audio signal received via the ADC 230 or a digital audio signal received from another component of the electronic device 101. For example, according to an embodiment, the audio signal processor 240 may perform changing a sampling rate, applying one or more filters, interpolation processing, amplifying or attenuating a whole or partial frequency bandwidth, noise processing (e.g., attenuating noise or echoes), changing channels (e.g., switching between mono and stereo), mixing, or extracting a specified signal for one or more digital audio signals. According to an embodiment, one or more functions of the audio signal processor 240 may be implemented in the form of an equalizer.

The DAC 250 may convert a digital audio signal into an analog audio signal. For example, according to an embodiment, the DAC 250 may convert a digital audio signal processed by the audio signal processor 240 or a digital audio signal obtained from another component (e.g., the processor (120) or the memory (130)) of the electronic device 101 into an analog audio signal.

The audio output mixer 260 may synthesize a plurality of audio signals, which are to be outputted, into at least one audio signal. For example, according to an embodiment, the audio output mixer 260 may synthesize an analog audio signal converted by the DAC 250 and another analog audio signal (e.g., an analog audio signal received via the audio input interface 210) into at least one analog audio signal.

The audio output interface 270 may output an analog audio signal converted by the DAC 250 or, additionally or alternatively, an analog audio signal synthesized by the audio output mixer 260 to the outside of the electronic device 101 via the sound output device 155. The sound output device 155 may include, for example, a speaker, such as a dynamic driver or a balanced armature driver, or a receiver. According to an embodiment, the sound output device 155 may include a plurality of speakers. In such a case, the audio output interface 270 may output audio signals having a plurality of different channels (e.g., stereo channels or 5.1 channels) via at least some of the plurality of speakers. According to an embodiment, the audio output interface 270 may be connected with the external electronic device 102 (e.g., an external speaker or a headset) directly via the connecting terminal 178 or wirelessly via the wireless communication module 192 to output an audio signal.

According to an embodiment, the audio module 170 may generate, without separately including the audio input mixer 220 or the audio output mixer 260, at least one digital audio signal by synthesizing a plurality of digital audio signals using at least one function of the audio signal processor 240.

According to an embodiment, the audio module 170 may include an audio amplifier (not shown) (e.g., a speaker amplifying circuit) that is capable of amplifying an analog audio signal inputted via the audio input interface 210 or an audio signal that is to be outputted via the audio output interface 270. According to an embodiment, the audio amplifier may be configured as a module separate from the audio module 170.

Figure 3:
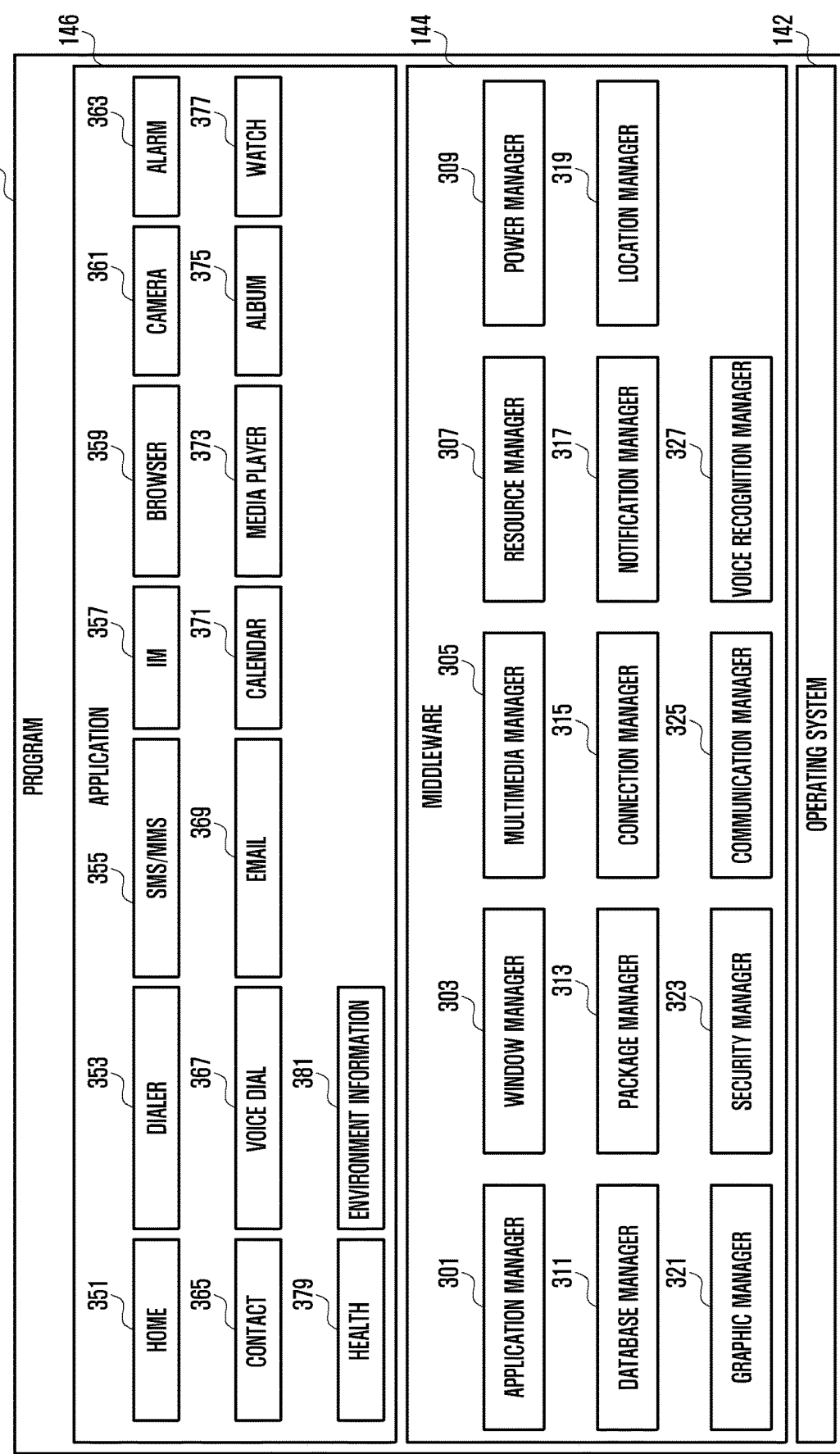
FIG. 3 is a block diagram illustrating a program according to various embodiments.

FIG. 3 is a block diagram 300 illustrating the program 140 according to various embodiments. According to an embodiment, the program 140 may include an operating system (OS) 142 to control one or more resources of the electronic device 101, middleware 144, or an application 146 executable in the OS 142. The OS 142 may include, for example, Android™, iOS™, Windows™, Symbian™, Tizen™, or Bada™. At least part of the program 140, for example, may be pre-loaded on the electronic device 101 during manufacture, or may be downloaded from or updated by an external electronic device (e.g., the electronic device 102 or 104, or the server 108) during use by a user.

The OS 142 may control management (e.g., allocating or deallocation) of one or more system resources (e.g., process, memory, or power source) of the electronic device 101. The OS 142, additionally or alternatively, may include one or more driver programs to drive other hardware devices of the electronic device 101, for example, the input device 150, the sound output device 155, the display device 160, the audio module 170, the sensor module 176, the interface 177, the haptic module 179, the camera module 180, the power management module 188, the battery 189, the communication module 190, the subscriber identification module 196, or the antenna module 197.

The middleware 144 may provide various functions to the application 146 such that a function or information provided from one or more resources of the electronic device 101 may be used by the application 146. The middleware 144 may include, for example, an application manager 301, a window manager 303, a multimedia manager 305, a resource manager 307, a power manager 309, a database manager 311, a package manager 313, a connectivity manager 315, a notification manager 317, a location manager 319, a graphic manager 321, a security manager 323, a telephony manager 325, or a voice recognition manager 327.

The application manager 301, for example, may manage the life cycle of the application 146. The window manager 303, for example, may manage one or more graphical user interface (GUI) resources that are used on a screen. The multimedia manager 305, for example, may identify one or more formats to be used to play media files, and may encode or decode a corresponding one of the media files using a codec appropriate for a corresponding format selected from the one or more formats. The resource manager 307, for example, may manage the source code of the application 146 or a memory space of the memory 130. The power manager 309, for example, may manage the capacity, temperature, or power of the battery 189, and determine or provide related information to be used for the operation of the electronic device 101 based at least in part on corresponding information of the capacity, temperature, or power of the battery 189. According to an embodiment, the power manager 309 may interwork with a basic input/output system (BIOS) (not shown) of the electronic device 101.

The database manager 311, for example, may generate, search, or change a database to be used by the application 146. The package manager 313, for example, may manage installation or update of an application that is distributed in the form of a package file. The connectivity manager 315, for example, may manage a wireless connection or a direct connection between the electronic device 101 and the external electronic device. The notification manager 317, for example, may provide a function to notify a user of an occurrence of a specified event (e.g., an incoming call, message, or alert). The location manager 319, for example, may manage locational information on the electronic device 101. The graphic manager 321, for example, may manage one or more graphic effects to be offered to a user or a user interface related to the one or more graphic effects.

The security manager 323, for example, may provide system security or user authentication. The telephony manager 325, for example, may manage a voice call function or a video call function provided by the electronic device 101. The voice recognition manager 327, for example, may transmit a user's voice data to the server 108, and receive, from the server 108, a command corresponding to a function to be executed on the electronic device 101 based at least in part on the voice data, or text data converted based at least in part on the voice data. According to an embodiment, the middleware 344 may dynamically delete some existing components or add new components. According to an embodiment, at least part of the middleware 144 may be included as part of the OS 142 or may be implemented as another software separate from the OS 142.

The application 146 may include, for example, a home 351, dialer 353, short message service (SMS)/multimedia messaging service (MMS) 355, instant message (IM) 357, browser 359, camera 361, alarm 363, contact 365, voice recognition 367, email 369, calendar 371, media player 373, album 375, watch 377, health 379 (e.g., for measuring the degree of workout or biometric information, such as blood sugar), or environmental information 381 (e.g., for measuring air pressure, humidity, or temperature information) application. According to an embodiment, the application 146 may further include an information exchanging application (not shown) that is capable of supporting information exchange between the electronic device 101 and the external electronic device. The information exchange application, for example, may include a notification relay application adapted to transfer designated information (e.g., a call, message, or alert) to the external electronic device or a device management application adapted to manage the external electronic device. The notification relay application may transfer notification information corresponding to an occurrence of a specified event (e.g., receipt of an email) at another application (e.g., the email application 369) of the electronic device 101 to the external electronic device. Additionally or alternatively, the notification relay application may receive notification information from the external electronic device and provide the notification information to a user of the electronic device 101.

The device management application may control the power (e.g., turn-on or turn-off) or the function (e.g., adjustment of brightness, resolution, or focus) of the external electronic device or some component thereof (e.g., a display device or a camera module of the external electronic device). The device management application, additionally or alternatively, may support installation, delete, or update of an application running on the external electronic device.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspects (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 4A:
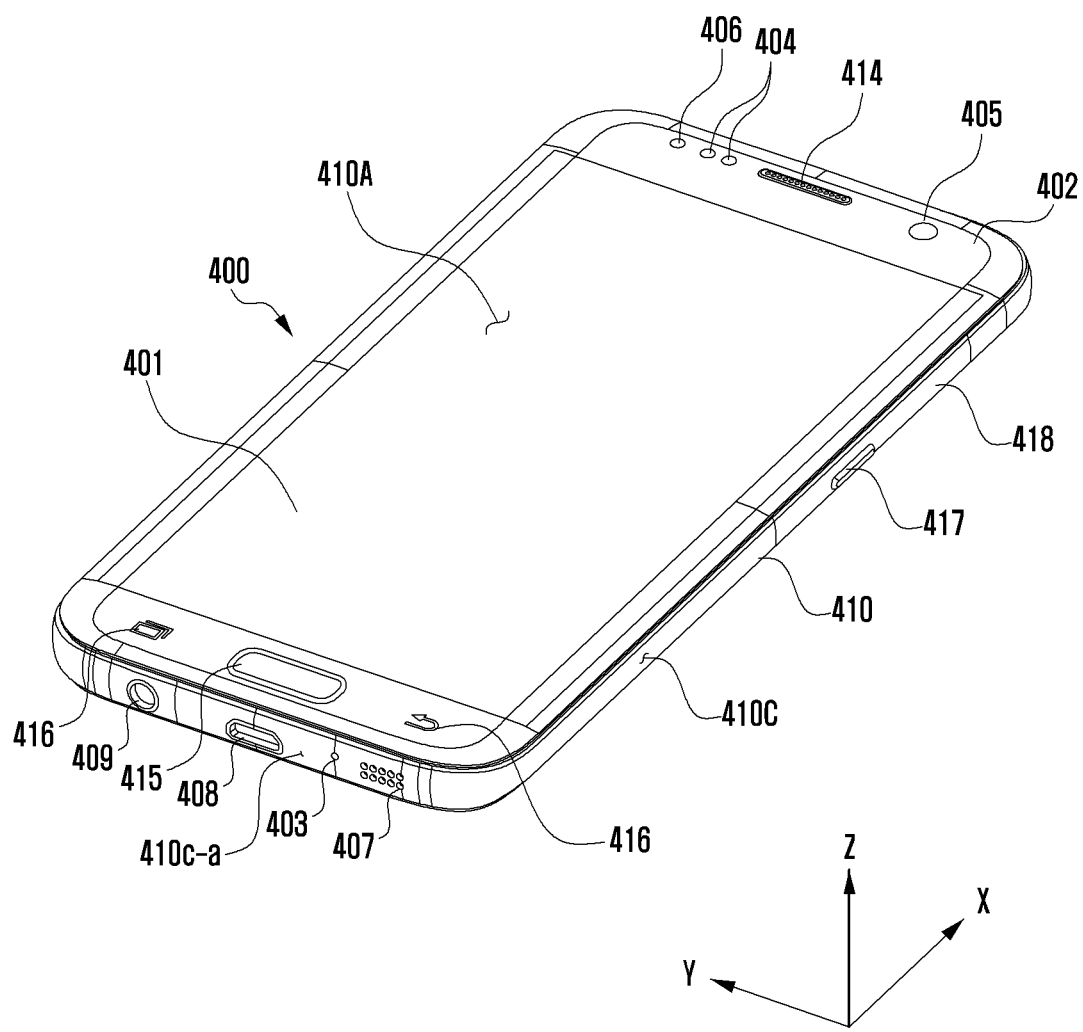
FIG. 4A is a perspective view showing a front side of a mobile electronic device according to an embodiment.
Figure 4B:
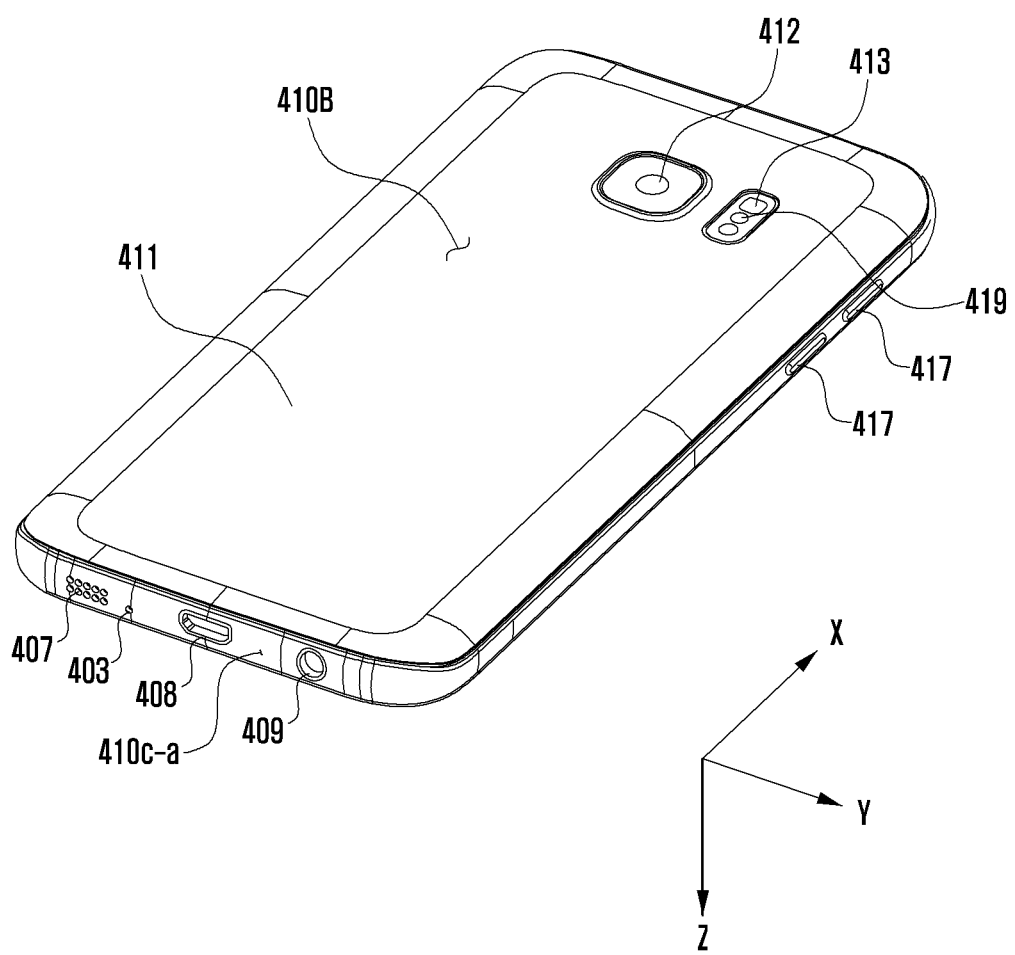
FIG. 4B is a perspective view showing a rear side of the electronic device of FIG. 4A.

FIG. 4A is a perspective view showing a front side of a mobile electronic device according to an embodiment. FIG. 4B is a perspective view showing a rear side of the electronic device of FIG. 4A, and FIG. 4C is a plan view showing an upper side of the electronic device of FIG. 4A.

As shown in FIGS. 4A, 4B, and 4C, an electronic device 400 (e.g., the electronic device 101 in FIG. 1) according to an embodiment may include a housing 410 that includes a first side (or a front side) 410A, a second side (or a rear side) 410B, and a lateral side 410C surrounding a space between the first side 410A and the second side 410B. In another embodiment (not shown), the housing may refer to a structure that forms a part of the first side 410A, second side 410B and lateral side 410C. According to one embodiment, the first side 410A may be formed by a front plate 402 (e.g., a glass plate having various coating layers, or a polymer plate) at least a part of which is substantially transparent. The second side 410B may be formed by a rear plate 411 which is substantially opaque. The rear plate 411 may be made of, for example, coated or colored glass, ceramic, polymer, metal (e.g., aluminum, stainless steel (STS), or magnesium), or a combination thereof. The lateral side 410C may be formed by a lateral bezel structure (or a lateral member) 418 which joins the front plate 402 and the rear plate 411 and may include a metal and/or polymer. In some embodiments, the rear plate 411 and the lateral bezel structures 418 may be integrally formed of the same material (e.g., a metal such as aluminum).

According to one embodiment, the electronic device 400 may include at least one of a display 401, audio modules 403, 407 and 414, sensor modules 404 and 419, camera modules 405, 412 and 413, key input devices 415, 416 and 417, an indicator 406, and connector holes 408 and 409. In some embodiments, at least one (e.g., the key input devices 415, 416 and 417, or the indicator 406) of the above components may be omitted from the electronic device 400, or one or more other components may be added in the electronic device 400.

The display 401 may be exposed through a substantial portion of the front plate 402. The display 401 may be associated with or adjacent to a touch sensing circuit, a pressure sensor capable of measuring the intensity of force incurred by a touch, and/or a digitizer for sensing a stylus pen using a magnetic field.

The audio modules 403, 407 and 414 may include microphone holes 403 and 421 and speaker holes 407 and 414. The microphone may be disposed inside the housing 410 (i.e., in the space between the first side 410A and the second side 410B) and acquire external sound through the microphone holes 403 and 421. In some embodiments, a plurality of microphones may be disposed in the housing 410 so as to detect the direction of sound. For example, a first microphone may acquire sound through the first microphone hole 403 formed on the lower side 410c-a (as shown in FIGS. 4A and 4B), and a second microphone may acquire sound through the second microphone hole 421 formed on the upper side 410c-b (as shown in FIG. 4C). The speaker holes 407 and 414 may include an external speaker hole 407 and a receiver hole 414 adapted to output a counterparty's voice during a call. In some embodiments, the speaker holes 407 and 414 and the microphone hole 403 may be implemented as a single hole, or the speaker (e.g., a piezo speaker) may be mounted in the electronic device 400 without the speaker holes 407 and 414.

The sensor modules 404 and 419 may generate electric signals or data value corresponding to various operational states or environmental states of the electronic device 400. The sensor modules 404 and 419 may include, for example, a first sensor module 404 (e.g., a proximity sensor), a second sensor module (not shown) (e.g., a fingerprint sensor), which are disposed on the first side 410A of the housing 410, and/or a third sensor module 419 (e.g., an heart rate monitor HRM sensor) disposed on the second side 410B of the housing 410. In addition, a fingerprint sensor may be disposed on the second side 410B or on the first side 410A of the housing 410 (e.g., on the home key button 415). Although not shown, the sensor module 419 may further include, for example, at least one of a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, a gas sensor (e.g., an electronic nose sensor), an illuminance sensor, etc. According to one embodiment, the gas sensor is disposed inside the housing 410 and is capable of detecting components of the air immediately outside the electronic device 400 through a hole (e.g., the first microphone hole 403 or 421, the speaker hole 407 or 414, or the connector hole 408 or 409) formed in the housing 410.

The camera modules 405, 412 and 413 may include a first camera device 405 disposed on the first side 410A, and a second camera device 412 and/or a flash 413 disposed on the second side 410B. Each of the camera devices 405 and 412 may include one or more lenses, an image sensor, and/or an image signal processor. The flash 413 may include, for example, a light emitting diode or a xenon lamp. In some embodiments, two or more lenses (wide angle and telephoto lenses) and image sensors may be disposed on one side of the electronic device 400.

The key input devices 415, 416 and 417 may include a home key button 415 disposed on the first surface 410A of the housing 410, touch pads 416 disposed near the home key button 415, and/or a side key button 417 disposed on the lateral side 410C of the housing 410. In another embodiment, the electronic device 400 may not include some or all of the above-mentioned key input devices 415, 416 and 417, and such excluded key input devices may be implemented in other form such as soft keys on the display 401.

The indicator 406 may be disposed on the first side 410A of the housing 410, for example. The indicator 406 may output status information of the electronic device 400 visually by, for example, providing a notification light, and may include an LED, for example.

The connector holes 408 and 409 may include a first connector hole 408 and a second connector hole 409. The first connector hole 408 is adapted to receive a connector 408 (e.g., a USB connector) for transmitting/receiving power and/or data to/from an external electronic device. The second connector hole 409 (e.g., an earphone jack) is adapted to receive a connector for transmitting/receiving audio signal to/from an external electronic device.

Figure 5:
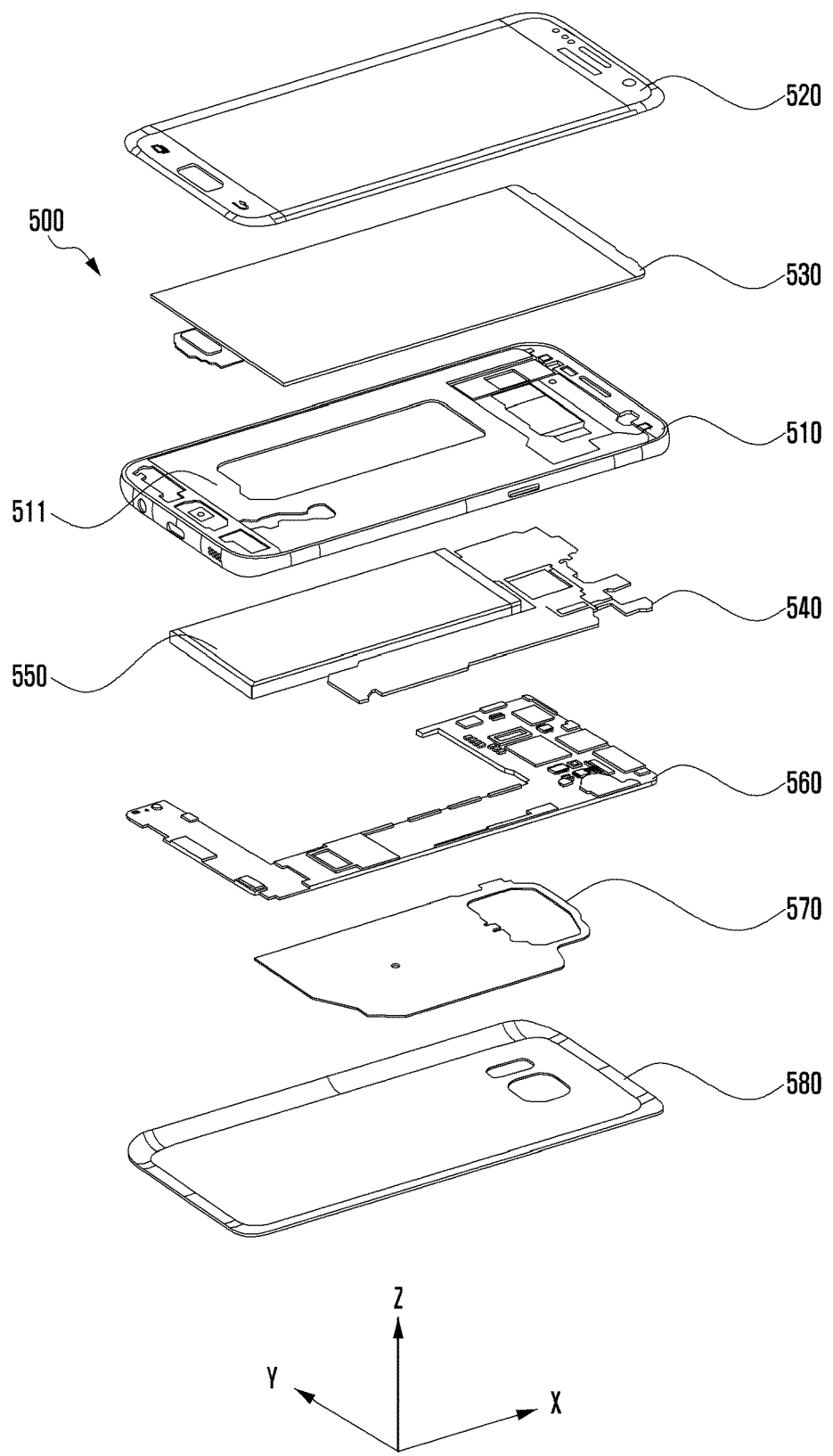
FIG. 5 is an exploded perspective view showing a mobile electronic device according to an embodiment.

FIG. 5 is an exploded perspective view showing a mobile electronic device according to an embodiment.

As shown in FIG. 5, an electronic device 500 (e.g., the electronic device 101 in FIG. 1 or the electronic device 400 of FIGS. 4A to 4C) may include a lateral bezel structure 510, a first support member 511 (e.g., a bracket), a front plate 520, a display 530, a printed circuit board 540, a battery 550, a second support member 560 (e.g., a rear case), an antenna 570, and a rear plate 580. In some embodiments, at least one (e.g., the first support member 511 or the second support member 560) of the above components may be omitted from the electronic device 500, or one or more other components may be added in the electronic device 500. At least one of the components of the electronic device 500 may be the same as or similar to the corresponding component(s) of the electronic device 400 previously described in FIGS. 4A to 4C, and detailed description of the same or similar component(s) will be omitted below.

The lateral bezel structure 510 may form a lateral side of the electronic device 500 (e.g., the lateral side 410C in FIG. 4A). The lateral bezel structure 510 may have one or more holes formed therein. Electronic components (e.g., a receiver, a speaker, a microphone, a sensor, a camera, and/or a connector) may be mounted on the lateral bezel structure 510 and fluidically communicate with the outside of the electronic device 500 through the hole(s) described in connection with FIGS. 4A-4C. Here, fluidic communication with the outside of the electronic device 500 may refer to exposure to the outside, contact with the outside air, or electrical (or physical) connection with an external electronic device.

The first support member 511 may be disposed inside the electronic device 500, being connected with or formed integrally with the lateral bezel structure 510. The first support member 511 may be formed of, for example, a metal material and/or a non-metal (e.g., polymer) material. The first support member 511 may be combined with the display 530 on one side thereof and combined with the printed circuit board 540 on the other side thereof. On the printed circuit board 540, a processor, a memory, and/or an interface may be mounted.

The processor may include, for example, one or more of a central processing unit, an application processor, a graphics processing unit, an image signal processor, a sensor hub processor, or a communication processor. The memory may include, for example, a volatile memory or a non-volatile memory. The interface may include, for example, a high definition multimedia interface (HDMI), a universal serial bus (USB) interface, an SD card interface, and/or an audio interface. The interface may electrically or physically connect the electronic device 500 with an external electronic device and may include a USB connector, an SD card/MMC connector, or an audio connector. The processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The battery 550, which is a device for supplying power to the components of the electronic device 500, may include a rechargeable secondary battery, a non-rechargeable tertiary battery, or a fuel cell. At least a portion of the battery 550 may be disposed substantially coplanar with the printed circuit board 540. The battery 550 may be disposed integrally with or detachably from the electronic device 500.

The antenna 570 may be disposed between the rear plate 580 and the battery 550. The antenna 570 may include, for example, a near field communication (NFC) antenna, a wireless charging antenna, and/or a magnetic secure transmission (MST) antenna. The antenna 570 may be used to perform short-range communication with an external device or wirelessly receive power required for charging. In other embodiments, part of the antenna structure may be the lateral bezel structure 510 and the first support member 511.

Figure 6B:
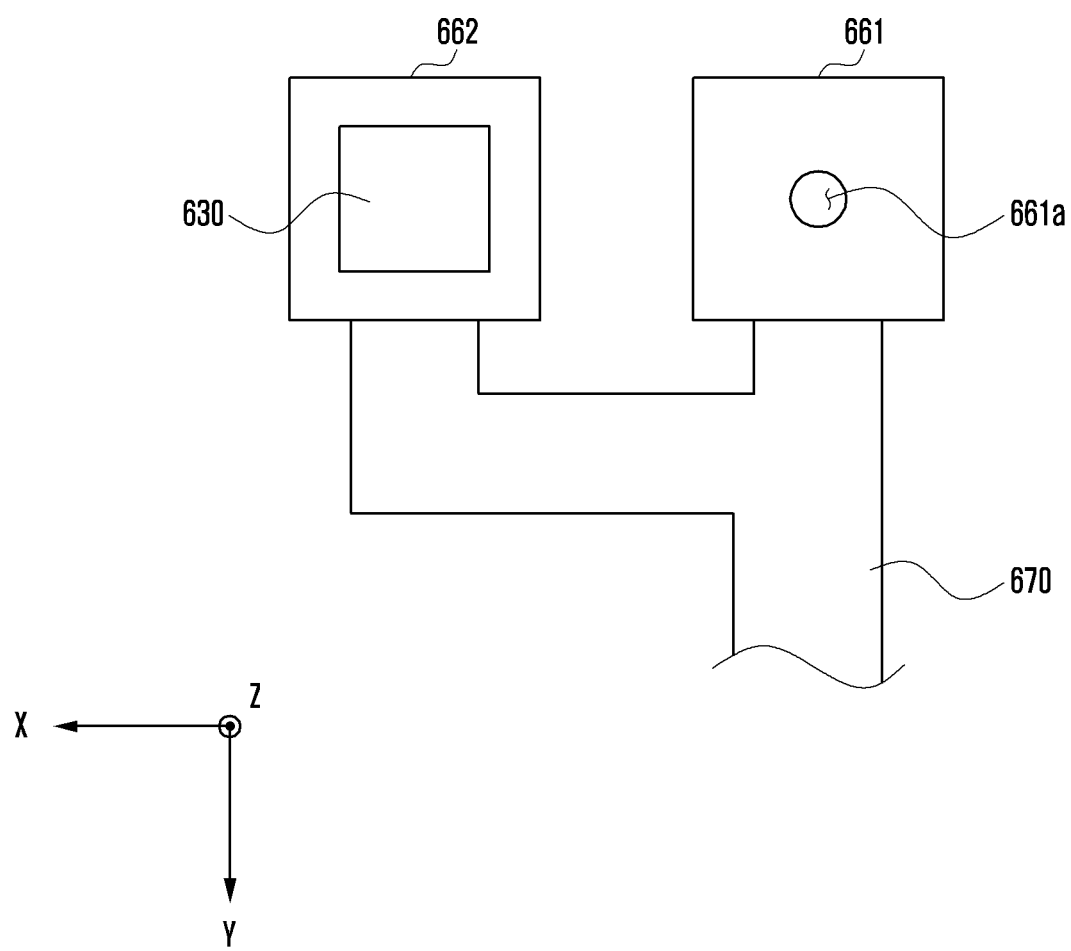
FIG. 6B is a schematic view showing one side of the structure shown in FIG. 6A.

FIG. 6A is a cross-sectional view showing a structure equipped with a microphone and a gas sensor according to an embodiment. FIG. 6B is a schematic view showing one side of the structure shown in FIG. 6A.

As shown in FIGS. 6A and 6B, a structure 600 according to an embodiment may include a bezel structure 610, a microphone 620, a gas sensor 630, attaching agents 641, 642 and 643, waterproof films 651 and 652, printed circuit boards (PCBs) 661 and 662, and a flexible PCB (FPCB) 670.

According to an embodiment, the bezel structure 610 may form a portion of the housing of the electronic device (e.g., the lateral bezel structure 418 in FIG. 4A or the lateral bezel structure 510 in FIG. 5).

According to an embodiment, a hole 612 (e.g., the first microphone hole 403 in FIG. 4A or the second microphone hole 421 in FIG. 4C) may be formed inward from a lateral side 611 of the bezel structure 610. The hole 612 may be utilized as an inlet for the external sound acquisition of the microphone located inside the housing. In addition, the hole 612 may be utilized as an inlet for the outside air acquisition of the gas sensor located inside the housing.

According to one embodiment, the hole 612 may be configured to include an outer opening 612a formed on the lateral side 611, first and second inner openings 612b and 612c formed in the rear side 613 of the bezel structure 610, a first passage 612d extending from the outer opening 612a in a direction (i.e., the X-axis direction shown in FIG. 6A) perpendicular to the lateral side 611 (i.e., parallel to the front side 614 or rear side 613 of the bezel structure 610), a second passage 612e connecting one point of the first passage 612d to the first inner opening 612b, and a third passage 612f connecting another point of the first passage 612d to the second inner opening 612c.

According to an embodiment, the microphone 620 may be disposed on the rear side 613 of the bezel structure 610 and may acquire sound from outside the electronic device through the hole 612. For example, one surface of the first PCB 661 may be attached to the rear side 613 of the bezel structure 610 using the first attaching agent 641 so as to cover the second passage 612e. The microphone 620 may be disposed on the other surface of the first PCB 661 opposite to the surface of the first PCB 661 that is attached to the rear side 613. The microphone 620 may include a first surface having an opening 621 formed thereon as an air passage, and a second surface opposite to the first surface. The first PCB 661 may have a via 661a formed therein as an air passage from one surface of the first PCB 661 to the other surface. The first surface of the microphone 620 may be disposed on the other surface of the first PCB 661 such that the opening 621 overlaps the via 661a. Accordingly, the microphone 620 may acquire sound from outside along the second passage 612e, through the via 661a and the opening 621.

According to an embodiment, the first attaching agent 641 may be a double-sided tape having waterproof characteristics. Thus, the first attaching agent 641 may prevent water or air from flowing into an inner space 680 of the electronic device through the second passage 612e.

According to an embodiment, the first waterproof film 651 may block the inflow of water into the microphone 620. For example, the first waterproof film 651 may be attached to a surface of the first PCB 661 so as to cover the via 661a. The first waterproof film 651 may prevent water from flowing into the via 661a, while permitting the flow of air.

According to an embodiment, the gas sensor 630 may be disposed on the rear side 613 of the bezel structure 610 and be in contact with air that flows through the hole 612. For example, the gas sensor 630 may include a first surface having an opening 631a formed thereon as an air passage, and a second surface opposite to the first surface. The second surface of the gas sensor 630 may be attached to one surface of the second PCB 662. The first surface formed with the opening 631a of the gas sensor 630 may be attached to the rear surface 613 of the bezel structure 610 using the second attaching agent 642 so that the opening 631a fluidically communicates with the third passage 612f. Accordingly, the gas sensor 630 may be in contact with air introduced through the third passage 612f and the opening 631a. Meanwhile, one side of the second PCB 662 may be attached to the rear side of the bezel structure 610 through the third attaching agent 643.

According to an embodiment, each of the second attaching agent 642 and the third attaching agent 643 may be a double-sided tape having waterproof characteristics. The second and third attaching agents 642 and 643 may prevent water from flowing into the inner space 680 through the third passage 612f.

According to an embodiment, the second waterproof film 652 may block the inflow of water into the gas sensor 630. For example, the second waterproof film 652 may be attached to the first surface of the gas sensor 630 having the opening 631a so as to cover the opening 631a. The second waterproof film 652 may prevent water from flowing into the opening 631a of the gas sensor 630, while permitting the flow of air.

According to an embodiment, the microphone 620 and the gas sensor 630 may be electrically connected to the processor. For example, the FPCB 670 may electrically connect the first PCB 661 and the second PCB 662 to a main board (e.g., 540 in FIG. 5) of the electronic device. Therefore, the microphone 620 and the gas sensor 630 may be electrically connected to the processor (e.g., an application processor or a sensor hub processor) mounted on the main board.

Figure 7A:
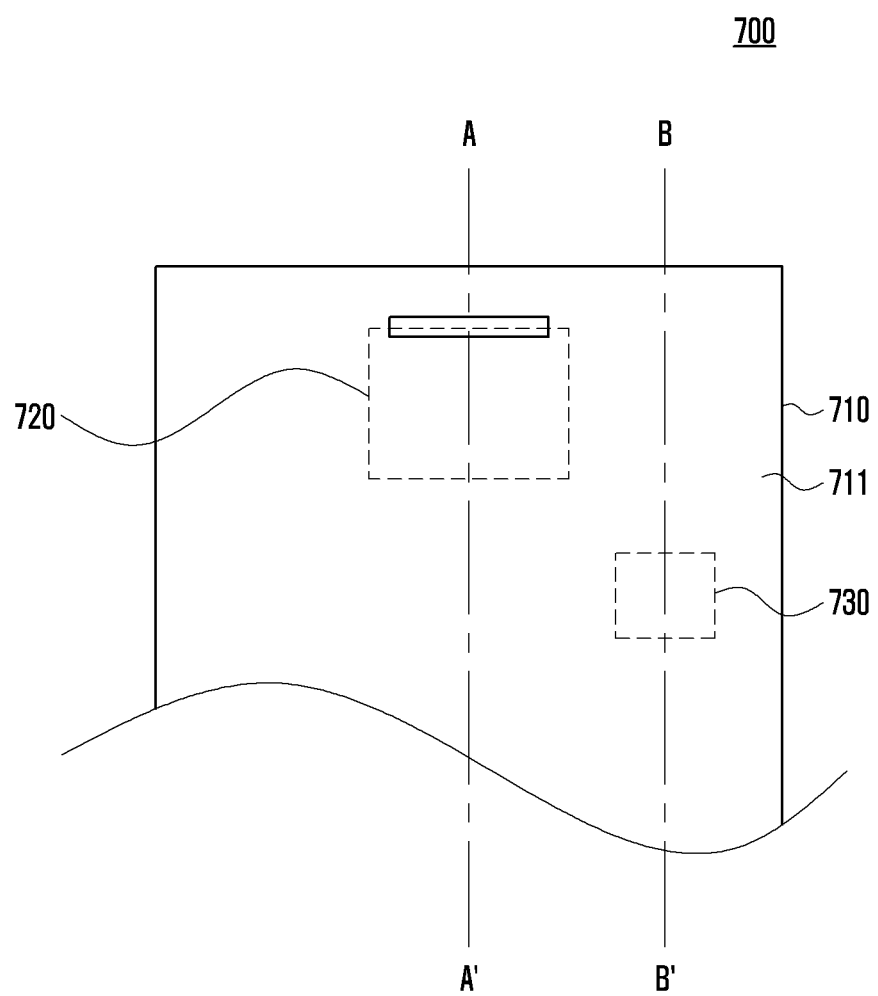
FIG. 7A is a schematic view showing a front side of a structure equipped with a receiver and a gas sensor according to an embodiment.
Figure 7B:
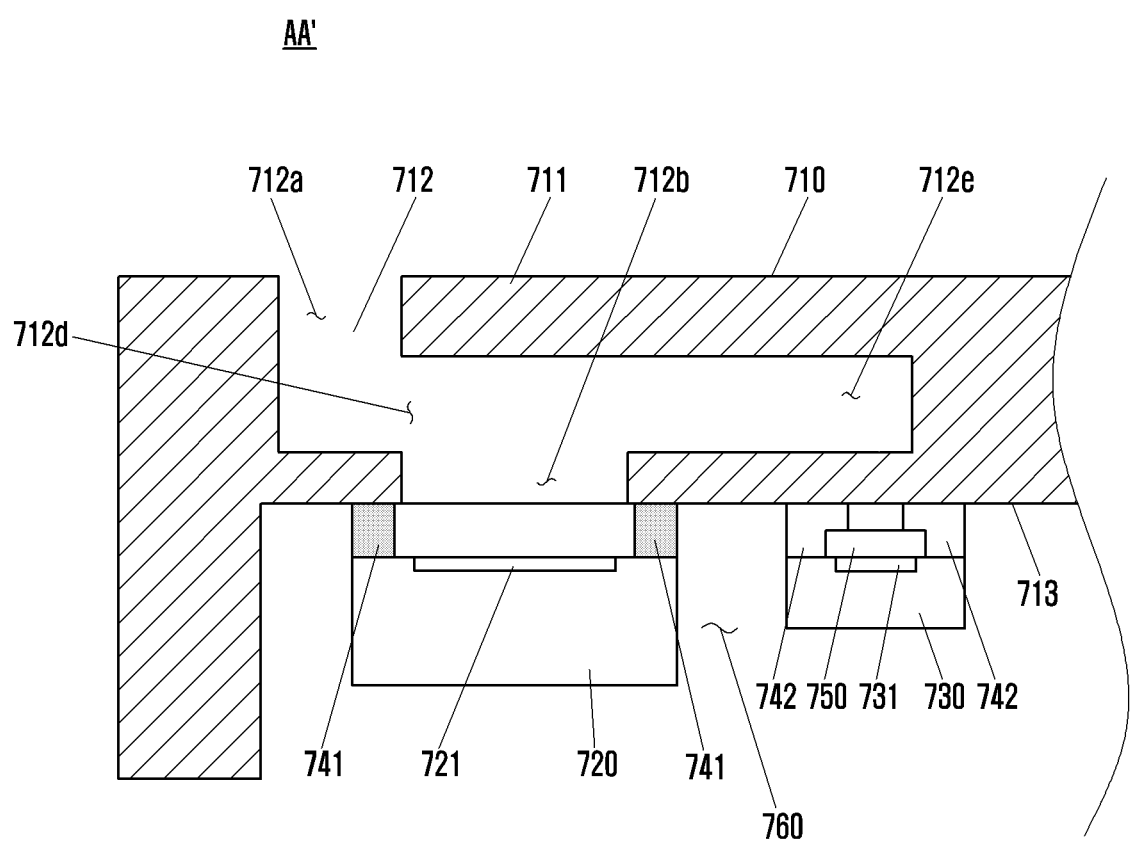
FIG. 7B is a cross-sectional view taken along the line AA' of FIG. 7A.
Figure 7C:
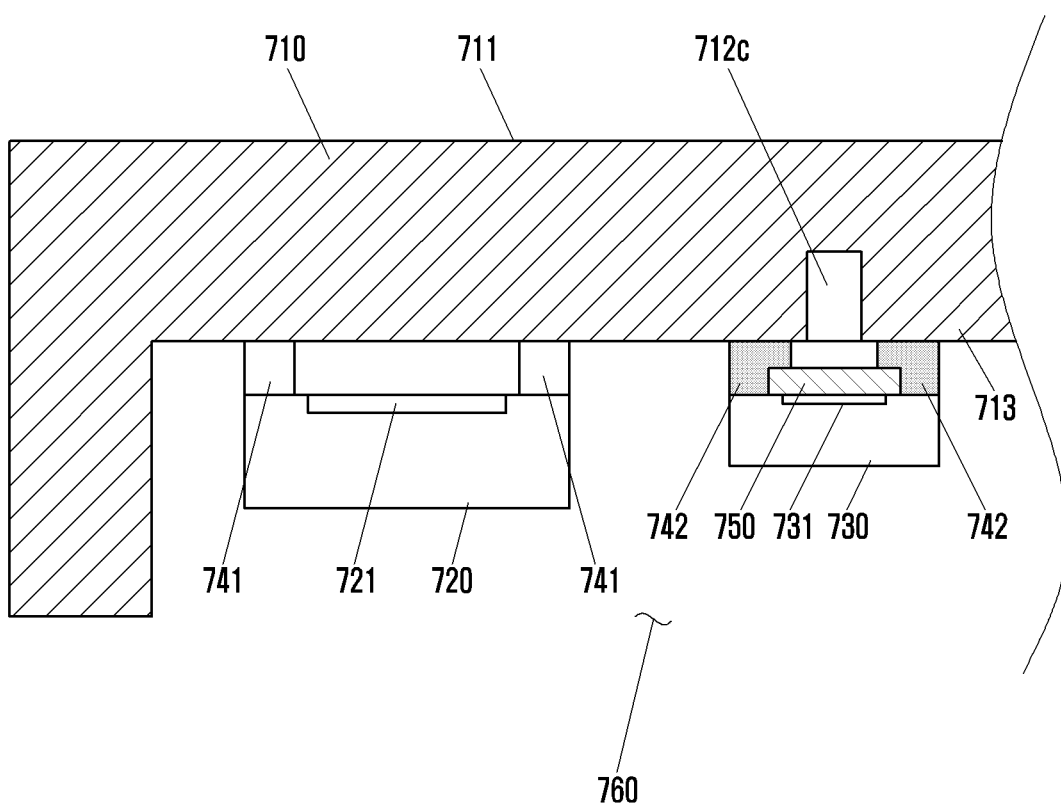
FIG. 7C is a cross-sectional view taken along the line BB' of FIG. 7A.

FIG. 7A is a schematic view showing a front side of a structure equipped with a receiver and a gas sensor according to an embodiment. FIG. 7B is a cross-sectional view taken along the line AA' of FIG. 7A, and FIG. 7C is a cross-sectional view taken along the line BB' of FIG. 7A.

As shown in FIG. 7, a structure 700 according to an embodiment may include a bezel structure 710, a receiver 720, a gas sensor 730, attaching agents 741 and 742, and a waterproof film 750.

According to an embodiment, the bezel structure 710 may form a portion of the housing of the electronic device (e.g., the first support member 511 in FIG. 5).

According to an embodiment, a hole 712 for both the receiver 720 and the gas sensor 730 may be formed inward from the upper side 711 of the bezel structure 710.

According to one embodiment, the hole 712 may be configured to include an outer opening 712a formed in the upper side 711 of the bezel structure 710, first and second inner openings 712b and 712c formed in the rear side 713 of the bezel structure 710, a first passageway 712d extended from the outer opening 712a to the first inner opening 712b, and a second passageway 712e extended from the first passageway 712d to the second inner opening 712c.

According to an embodiment, the receiver 720 may be disposed on the rear side 713 of the bezel structure 710 and output sound through the hole 712. For example, the receiver 720 may be disposed on the rear side 713 of the bezel structure 710 such that an opening 721 thereof faces the first inner opening 712b. The receiver 720 may be attached to the rear side 713 of the bezel structure 710 using the first attaching agent 741.

According to an embodiment, the first attaching agent 741 may be a double-sided tape having waterproof characteristics. The first attaching agent 741 may prevent external water or air from flowing into the inner space 760 of the electronic device through the hole 712.

According to an embodiment, the gas sensor 730 may be disposed on the rear side 713 of the bezel structure 710 and be in contact with outside air through the hole 712. For example, the gas sensor 730 may be disposed on the rear side 713 of the bezel structure 710 such that a surface formed with an opening 731 faces the second inner opening 712c. The gas sensor 730 may be attached to the rear side 713 of the bezel structure 710 using the second attaching agent 742.

According to an embodiment, the second attaching agent 742 may be a double-sided tape having waterproof characteristics. The second attaching agent 742 may prevent water or air from flowing into the inner space 760 through the hole 712.

According to an embodiment, the waterproof film 750 may block the inflow of water into the gas sensor 730. For example, the waterproof film 750 may be attached to the surface of the gas sensor 730 having the opening 731 so as to cover the opening 731. The waterproof film 750 may prevent water from flowing into the opening 731 of the gas sensor 730, while permitting the flow of air.

FIG. 8 is a cross-sectional view showing a structure equipped with a receiver and a gas sensor according to an embodiment.

As shown in FIG. 8, a structure 800 according to an embodiment may include a bezel structure 800, a receiver 820, a gas sensor 830, attaching agents 841, 842 and 843, a waterproof film 850, and a shielding sheet 860.

According to an embodiment, the bezel structure 800 may form a portion of the housing of the electronic device (e.g., the first support member 511 in FIG. 5).

According to an embodiment, a first hole 812 may be formed inward from the upper side 811 of the bezel structure 800. The first hole 812 may be utilized as an outlet for the sound output of the receiver 820 located inside the housing. Also, the first hole 812 may be utilized as an air inlet for the gas sensor 830 located inside the housing.

According to an embodiment, one or more additional holes for directing the air flowing from the first hole 812 toward the gas sensor 830 may be formed.

According to one embodiment, a second hole 813 and a third hole 814 may be formed inward from the upper side 810 of the bezel structure 800 so as to direct the air introduced through the first hole 812 toward the gas sensor 830. In addition, the shielding sheet 860 may be disposed on the upper side 810 of the bezel structure 800 so as to form a passage 815 between the second and third holes 813 and 814. Therefore, the air introduced through the first hole 812 may flow to the gas sensor 830 through the second hole 813, the passage 815, and the third hole 814.

According to one embodiment, the shielding sheet 860 may be attached to the upper side 811 of the bezel structure 800 using the third attaching agent 843. In addition, the shielding sheet 860 may be made of, for example, a conductive material, and may dampen the sound outputted by the receiver 820 through the second hole 813.

According to an embodiment, the receiver 820 may be disposed on the rear side 817 of the bezel structure 800 and output sound through the first hole 812. For example, the receiver 820 may be disposed on the rear side 817 of the bezel structure 800 such that an opening 821 thereof faces the first hole 812. The receiver 820 may be attached to the rear side 817 of the bezel structure 800 using the first attaching agent 841.

According to an embodiment, the first attaching agent 841 may be a double-sided tape having waterproof characteristics. The first attaching agent 841 may prevent external water or air from flowing into the inner space 870 of the electronic device through the first hole 812.

According to an embodiment, the gas sensor 830 may be disposed on the rear side 817 of the bezel structure 800 and be in contact with air flowing through the first hole 812. For example, the gas sensor 830 may be disposed on the rear side 817 of the bezel structure 800 such that a surface formed with an opening 831 faces the third hole 814. The gas sensor 830 may be attached to the rear side 817 of the bezel structure 800 using the second attaching agent 842.

According to an embodiment, the second attaching agent 842 may be a double-sided tape having waterproof characteristics. The second attaching agent 842 may prevent water or air from flowing into the inner space 870 through the third hole 814.

According to an embodiment, the waterproof film 850 may block the inflow of water into the gas sensor 830. For example, the waterproof film 850 may be attached to the surface of the gas sensor 830 formed with the opening 831 so as to cover the opening 831. The waterproof film 850 may prevent water from flowing into the opening 831 of the gas sensor 830, while permitting the flow of air.

Figure 9:
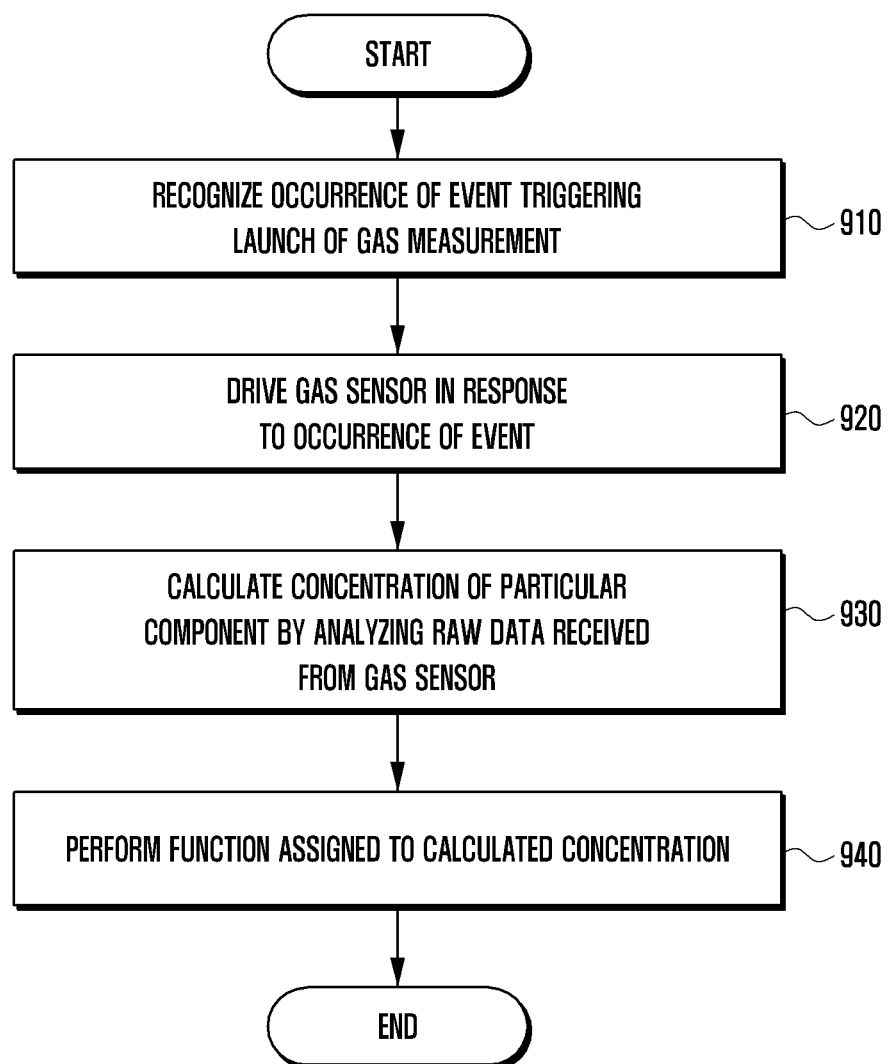
FIG. 9 is a flow diagram illustrating operations of an electronic device having a gas sensor according to an embodiment.

FIG. 9 is a flow diagram illustrating operations of an electronic device having a gas sensor according to an embodiment.

The operations shown in FIG. 9 and described hereinafter may be performed by a processor (e.g., the processor 120 in FIG. 1) of the electronic device having the structure described above with reference to FIG. 6A-B, 7A-C, or 8.

According to an embodiment, at operation 910, the processor may recognize the occurrence of an event that triggers a launch (i.e., initiation) of gas measurement.

In one embodiment, the event may be a specified time (e.g., 1:00 p.m.). That is, at the specified time, the processor may recognize that the event occurs.

In another embodiment, the event may be a designated place (e.g., home). For example, the processor may acquire position information of the electronic device through the wireless communication module (e.g., module 192 in FIG. 1). When the acquired position information corresponds to the designated place, that is, when the electronic device is located at the designated place, the processor may recognize that the event occurs.

In still another embodiment, the event may be a user input of triggering a gas measurement. For example, the user input may be a user's touch that selects a measurement start button displayed on the display. Also, the user input may be a user's voice, received via the microphone, requesting gas measurement.

In yet another embodiment, the event may be a call request signal received from or transmitted to a counterparty via the wireless communication module (e.g., module 192 of FIG. 1). That is, the processor may detect the reception or transmission of the call request signal and recognize that as the occurrence of the event. For example, in the electronic device having a common hole for the microphone and the gas sensor as shown in FIGS. 6A-6B, the processor may recognize a call request signal as an event for starting a measurement of the user's health status (e.g., blood alcohol concentration, halitosis, etc.) using the gas sensor.

In yet another embodiment, the user's reaction to the reception of the call request signal may be recognized as the occurrence of the event for initiating the measurement of the user's health status using the gas sensor. For example, in response to receiving the call request signal, the processor may output a specific notification sound through the speaker, display a popup window or message through the display, and/or output a vibration through the haptic module. When the user accepts the call, it may be recognized as the event. In this case, the user input to accept the call, such as touch or voice, may be received via input devices such as the touch-sensitive display or the microphone.

In yet another embodiment, a user input of triggering the transmission of the call request signal may be recognized as the event for initiating the measurement of the user's health status using the gas sensor. For example, this user input may be a user's touch of selecting a call button displayed on the display, or a user's voice, received via the microphone, of requesting a call connection.

According to an embodiment, at operation 920, the processor may drive the gas sensor in response to the occurrence of the event. For example, the processor may control the gas sensor to acquire data associated with a particular component of the air in contact with the gas sensor. Then, the gas sensor may deliver the acquired raw data to the processor (e.g., the sensor hub processor).

In one embodiment, the processor may further drive a temperature/humidity sensor in response to the occurrence of the event. Then, the temperature/humidity sensor may generate temperature/humidity raw data and transmit the generated data to the processor.

According to an embodiment, at operation 930, the processor (e.g., the sensor hub processor) may analyze the raw data received from the gas sensor and thereby calculate the concentration (e.g., parts per million (ppm), $mg/m^3$, or $ug/m^3$) of a particular component of the air such as alcohol, volatile organic compounds (VOC), total VOC (TVOC), fine dust, carbon dioxide, halitosis (e.g., volatile sulfur compounds (VSC)), etc.

In one embodiment, the processor may calculate temperature/humidity by analyzing the raw data received from the temperature/humidity sensor and modify the calculated concentration based on the calculated temperature/humidity.

According to an embodiment, at operation 940, the processor may perform a particular function assigned to the calculated or modified concentration.

In one embodiment, the operation 940 may include an operation of notifying the quality of the outside air to the user. The outside air quality may be classified into, for example, five levels (e.g., excellent, good, normal, poor, very bad), and the processor may output a notification message indicating the level corresponding to the calculated or modified concentration through the display and/or the speaker.

In one embodiment, the operation 940 may include an operation of notifying a blood alcohol concentration or a halitosis level to the user. For example, the processor may output an alert message via the display and/or the speaker when the blood alcohol concentration exceeds a predetermined value (e.g., a value corresponding to the legal driving limit).

In one embodiment, the operation 940 may include an operation of controlling, based on the calculated or modified concentration, the power-on/off or a specific function of an external electronic device (e.g., an internet of things (IoT) device) connected to the electronic device via the wireless communication module. For example, the processor may send a shutdown command to a vehicle's electronic control system when the blood alcohol concentration exceeds the predetermined value. As another example, the processor may control an air purifier, an air conditioner, a heater, a humidifier, a dehumidifier, etc., to improve air quality, when the air quality is low.

In one embodiment, the operation 940 may include an operation of adjusting a measurement cycle of the gas sensor, based on the calculated or modified concentration. For example, as shown in Table 1, the processor may reduce power consumption by increasing the measurement cycle as the air quality improves.

TABLE 1

| Concentration of TVOC | Air Quality | Measurement Cycle |
|---|---|---|
| Level 1 (TVOC < 0.3 $mg/m^3$) | Excellent | Once per 30 sec. |
| Level 2 (TVOC > 0.3 $mg/m^3$) | Good | Once per 20 sec. |
| Level 3 (TVOC > 3 $mg/m^3$) | Normal | Once per 10 sec. |
| Level 4 (TVOC > 10 $mg/m^3$) | Poor | Once per 5 sec. |
| Level 5 (TVOC > 25 $mg/m^3$) | Very bad | Once per 3 sec. |

In one embodiment, the operation 940 may include an operation of notifying the calculated concentration, a variation thereof, or corresponding information to an external entity (e.g., the user and/or an external electronic device). For example, when the air quality is changed, an alarm message may be outputted through the display and/or the speaker. When the air quality changes abruptly (e.g., a change from level 1 to level 5 within a few minutes as shown in Table 1), the processor may output a predetermined message (e.g., a fire alarm) corresponding to such a change via the display and/or the speaker. Also, the processor may send such a message to a nearby fire station.

Figure 10:
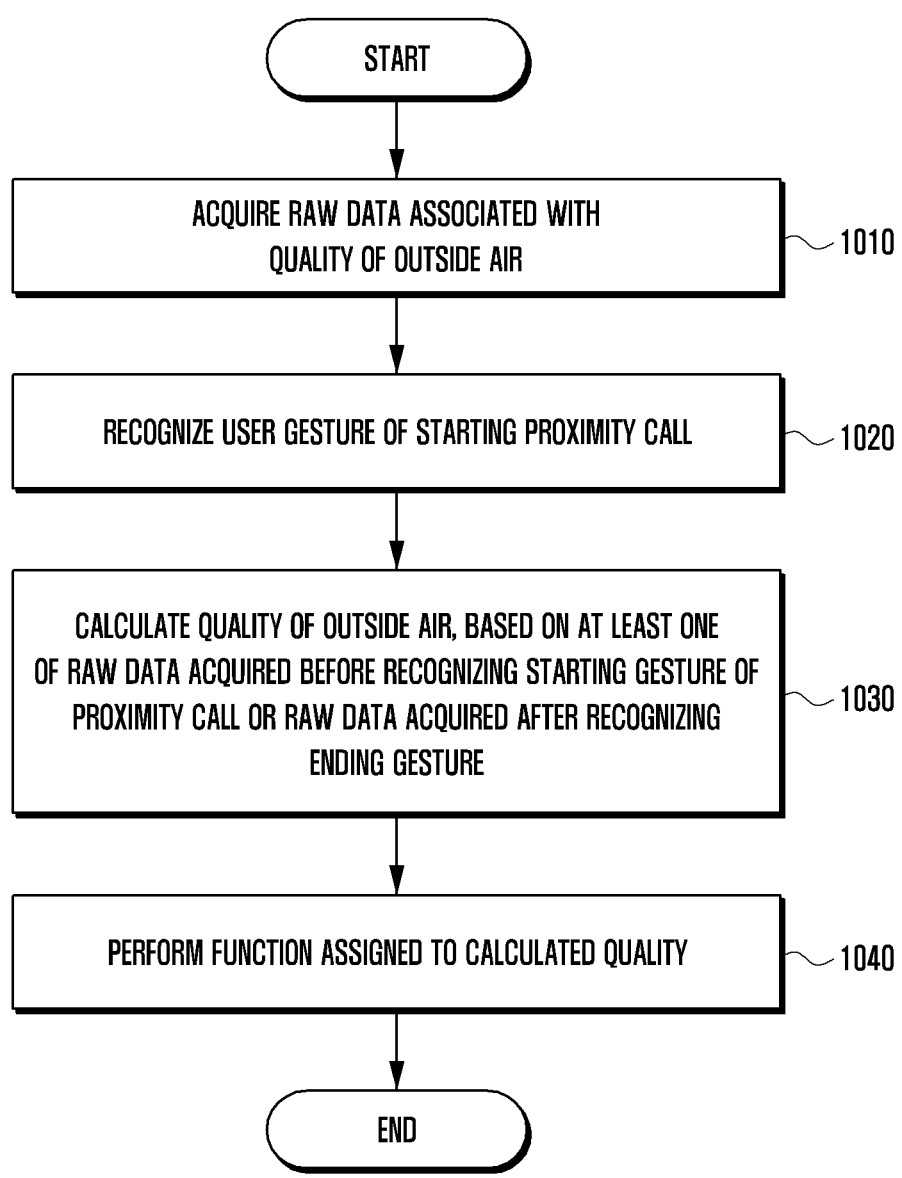
FIG. 10 is a flow diagram illustrating operations of an electronic device having a gas sensor according to an embodiment.

FIG. 10 is a flow diagram illustrating operations of an electronic device having a gas sensor according to an embodiment.

The operations shown in FIG. 10 and described hereinafter may be performed by a processor (e.g., the processor 120 in FIG. 1) of the electronic device having the structure described above with reference to FIG. 6A-B, 7A-C, or 8.

Normally, raw data acquired during a proximity call may result in an inaccurate calculation of air quality. Here, proximity calls refer to when the user talks into the electronic device while placing his/her ear in contact with or close to the receiver. For example, in the electronic device having a common hole for the microphone and the gas sensor as shown in FIGS. 6A-B, the gas sensor may detect air in the external environment mixed with air emitted from the user's mouth during the proximity call. This may cause inaccuracy in calculating the air quality of the outside environment. As another example, in the electronic device having a common hole for the receiver and the gas sensor as shown in FIG. 7 or 8, the inflow of air into the common hole may be disturbed by the user's ear which is in close contact with the receiver during the proximity call. Therefore, the calculation of the outside air quality may be inaccurate.

According to an embodiment of the present disclosure, the processor may perform a gas measurement operation (e.g., the following operations) while taking into account the proximity call.

According to an embodiment, at operation 1010, the processor may control the gas sensor to acquire raw data associated with outside air quality.

According to an embodiment, at operation 1020, the processor may recognize a user gesture of starting the proximity call while the gas sensor acquires raw data. In one embodiment, the processor may recognize the user gesture based on at least data obtained from a proximity sensor. For example, in a certain state (e.g., after a call request signal is received from or transmitted to an external device via the wireless communication module, or during a call with an external device via the wireless communication module), a data value obtained from the proximity sensor may indicate that the user has moved the electronic device closer to the user's face (e.g. cheek). In this case, the processor may recognize that a user gesture of starting the proximity call has occurred. Thereafter, when a data value obtained from the proximity sensor indicates the user has moved the electronic device away from the user's face by at least a predetermine distance, the processor may recognize that a user gesture of terminating the proximity call has occurred.

According to an embodiment, at operation 1030, the processor may calculate the outside air quality based on at least one of raw data acquired by the gas sensor before the user gesture of starting the proximity call is recognized, or raw data acquired by the gas sensor after the user gesture of ending the proximity call is recognized. For example, the processor may calculate the average value of raw data collected during a given time interval and then calculate the air quality by using the average value. In this calculation of the average value, raw data collected during the proximity call may be excluded. Alternatively, the operation of collecting raw data (e.g., storing raw data in the memory) may be interrupted during the proximity call and resumed at the end of the proximity call.

According to some embodiments, in the electronic device having a common hole for the microphone and the gas sensor as shown in FIGS. 6A-B, the raw data collected during the proximity call may not be discarded and be used in measuring the user's health status. Additionally, the processor may modify the calculated air quality, based on the temperature/humidity acquired via the temperature/humidity sensor.

According to an embodiment, at operation 1040, the processor may perform a particular function assigned to the calculated or modified air quality. For example, the operation 1040 may include an operation of notifying the user of the outside air quality, an operation of controlling the power-on/off or function of an external electronic device (e.g., an IoT device) based on the air quality, an operation of adjusting the measurement cycle of the gas sensor based on the air quality, or an operation of notifying a variation of air quality or transmitting corresponding information to an external entity (e.g., an external electronic device).

Figure 11:
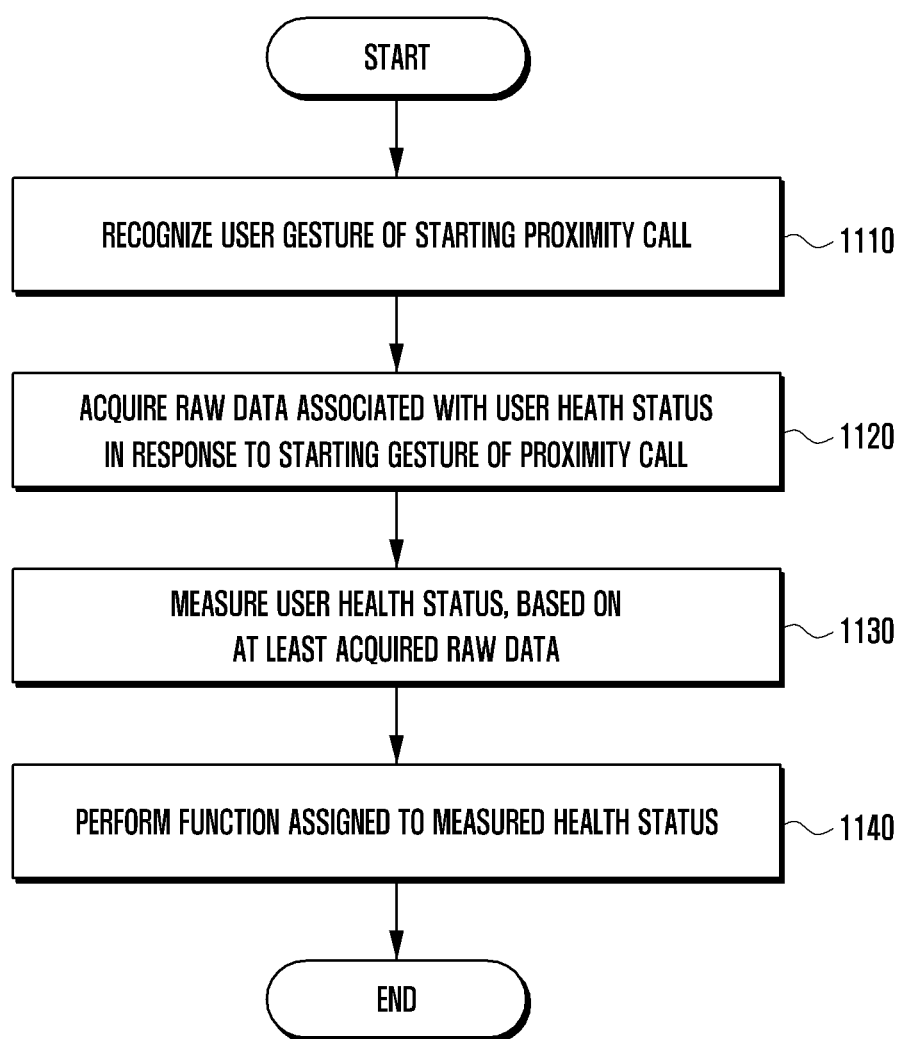
FIG. 11 is a flow diagram illustrating operations of an electronic device having a common hole for a microphone and a gas sensor according to an embodiment.

FIG. 11 is a flow diagram illustrating operations of an electronic device having a common hole for a microphone and a gas sensor according to an embodiment.

The operations shown in FIG. 11 and described hereinafter may be performed by a processor (e.g., the processor 120 in FIG. 1) of the electronic device having the structure described above with reference to FIGS. 6A-B.

According to an embodiment, at operation 1110, the processor may recognize a user gesture of starting a proximity call. In one embodiment, the processor may recognize the proximity call starting gesture based on at least data obtained from at least one sensor (e.g., the acceleration sensor, the proximity sensor, etc.).

According to an embodiment, at operation 1120, the processor may control the gas sensor to acquire raw data associated with the user's health status in response to the user gesture of starting the proximity call. In one embodiment, the acquisition of raw data may continue for a predetermined time after the proximity call starting gesture is recognized. In another embodiment, the acquisition of raw data may continue until the user gesture of ending the proximity call is recognized.

According to an embodiment, at operation 1130, the processor may measure the user's health status (e.g., blood alcohol concentration or halitosis level), based on at least the raw data obtained by the gas sensor after the proximity call starting gesture is recognized. Additionally, the processor may modify the measured health status, based on the temperature/humidity obtained through the temperature/humidity sensor.

According to an embodiment, at operation 1140, the processor may perform a particular function assigned to the measured or modified health status. For example, the operation 1140 may include an operation of notifying the blood alcohol concentration or halitosis level to the user, an operation of controlling the power-on/off or function of an external electronic device (e.g., an IoT device) based on the health status, an operation of adjusting the measurement cycle of the gas sensor based on the health status, or an operation of notifying a variation of health status or transmitting corresponding information to an external entity (e.g., an external electronic device).

Figure 12:
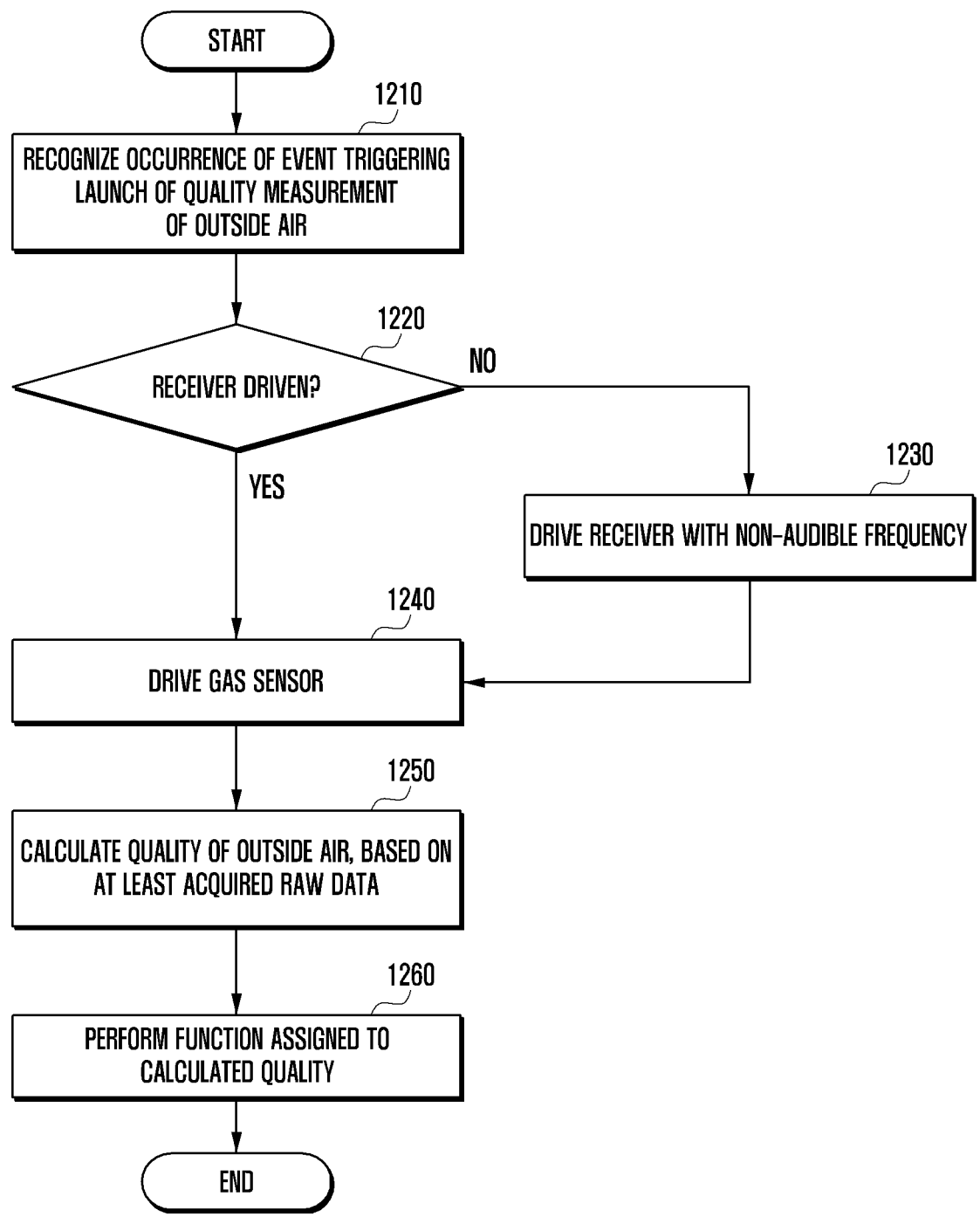
FIG. 12 is a flow diagram illustrating operations of an electronic device having a common hole for a receiver and a gas sensor according to an embodiment.

FIG. 12 is a flow diagram illustrating operations of an electronic device having a common hole for a receiver and a gas sensor according to an embodiment.

The operations shown in FIG. 12 and described hereinafter may be performed by a processor (e.g., the processor 120 in FIG. 1) of the electronic device having the structure described above with reference to FIG. 7A-C or 8.

According to an embodiment, at operation 1210, the processor may recognize the occurrence of an event that triggers the initiation of air quality measurement.

In one embodiment, the event may be a specified time (e.g., 1:00 p.m.). That is, at the specified time, the processor may recognize that the event occurs.

In another embodiment, the event may be a designated place (e.g., home). For example, the processor may acquire position information of the electronic device through the wireless communication module (e.g., module 192 in FIG. 1). When the acquired position information corresponds to the designated place, that is, when the electronic device is located at the designated place, the processor may recognize that the event occurs.

In still another embodiment, the event may be a user input of triggering an air quality measurement. For example, the user input may be a user's touch that selects a measurement start button displayed on the display. Also, the user input may be a user's voice, received via the microphone, requesting an air quality measurement.

According to an embodiment, at operation 1220, the processor may determine whether the receiver is driven. In one embodiment, driving may mean a state in which a voice signal obtained through the wireless communication module is converted into a sound wave and is being outputted through the receiver. When the receiver is not driven, the processor may drive, at operation 1230, the receiver to output a non-audible frequency signal (e.g., an ultrasonic signal). Since the flow of air may be guided to the gas sensor by sound outputted from the receiver, both at audible frequencies and non-audible frequencies, reaction rate and recovery speed of the gas sensor during air quality measurement may be improved when the receiver is driven.

According to an embodiment, at operation 1240, the processor may drive the gas sensor in response to the occurrence of the event or after driving the receiver at operation 1230. For example, the processor may control the gas sensor to acquire raw data associated with a particular component of the outside air. Then, the gas sensor may deliver the acquired raw data to the processor (e.g., the sensor hub processor). In addition, the processor may also drive the temperature/humidity sensor in response to the occurrence of the event.

According to an embodiment, at operation 1250, the processor (e.g., the sensor hub processor) may calculate the quality of the outside air, based on at least the raw data acquired by the gas sensor. In one embodiment, the proximity call as described above with reference to FIG. 10 may be considered in the calculation of the air quality because raw data obtained during the proximity call may result in inaccuracies in the air quality calculation. Additionally, the processor may analyze raw data received from the temperature/humidity sensor, thereby calculate the temperature/humidity, and modify the calculated air quality based on the calculated temperature/humidity.

According to an embodiment, at operation 1260, the processor may perform a particular function assigned to the calculated or modified air quality. For example, the operation 1260 may include an operation of notifying the outside air quality to the user, an operation of controlling the power-on/off or function of an external electronic device (e.g., an IoT device) based on the air quality, an operation of adjusting the measurement cycle of the gas sensor based on the air quality, or an operation of notifying a variation of air quality or transmitting corresponding information to an external entity (e.g., an external electronic device).

According to an embodiment of the present disclosure, an electronic device may comprise a housing having a hole formed therein; an audio device located inside the housing and communicating with an outside of the electronic device through the hole; a gas sensor located inside the housing and communicating with the outside through the hole; a proximity sensor located inside the housing; a wireless communication module located inside the housing; and a processor located inside the housing and electrically connected to the audio device, the gas sensor, the proximity sensor, and the wireless communication module. The processor may be configured to acquire data associated with air outside the electronic device by using the gas sensor, to recognize a user gesture of starting a proximity call by using the proximity sensor, and to calculate air quality based on at least one of data acquired by the gas sensor before the proximity call starting gesture is recognized and data acquired by the gas sensor after a gesture of ending the proximity call is recognized.

The audio device may include a microphone, and the housing may include a first side facing a first direction, a second side facing a second direction opposite to the first direction, and a structure surrounding at least a portion of a space between the first side and the second side. The hole may include an outer opening formed in a front side of the structure, first and second inner openings formed in a rear side of the structure, and a passage extended from the outer opening to the first and second inner openings. The microphone may be disposed on the rear side of the structure so as to allow air to flow into an opening of the microphone through the first inner opening. The gas sensor may be disposed on the rear side of the structure so as to allow air to flow into an opening of the gas sensor through the second inner opening.

The electronic device may further comprise an attaching agent disposed around the first and second inner openings and configured to prevent a foreign matter from flowing into the space through the first and second inner openings.

The electronic device may further comprise a first waterproof film attached to the opening of the microphone, and a second waterproof film attached to the opening of the gas sensor.

The processor may be further configured to drive the gas sensor when sound is acquired through the microphone.

The electronic device may further comprise a display electrically connected to the processor, and the processor may be further configured to output information associated with the calculated air quality through at least one of the display or the wireless communication module.

The processor may be further configured to drive the gas sensor during the proximity call.

The audio device may include a receiver, and the housing may include a first side facing a first direction, a second side facing a second direction opposite to the first direction, and a structure surrounding at least a portion of a space between the first side and the second side. The hole may include an outer opening formed in a front side of the structure, first and second inner openings formed in a rear side of the structure, and a passage extended from the outer opening to the first and second inner openings. The receiver may be disposed on the rear side of the structure so as to allow air to flow into an opening of the receiver through the first inner opening. The gas sensor may be disposed on the rear side of the structure so as to allow air to flow into an opening of the gas sensor through the second inner opening.

The electronic device may further comprise an attaching agent disposed around the first and second inner openings and configured to prevent a foreign matter from flowing into the space through the first and second inner openings.

The electronic device may further comprise a first waterproof film attached to the opening of the receiver, and a second waterproof film attached to the opening of the gas sensor.

The processor may be further configured to drive the gas sensor when the receiver is driven.

The processor may be further configured to control the receiver to output ultrasonic waves in response to occurrence of an event triggering an initiation of gas measurement using the gas sensor when the receiver is not driven.

The processor may be further configured to drive the gas sensor when position information acquired through the wireless communication module corresponds to a designated place.

The electronic device may further comprise a display electrically connected to the processor, wherein the processor may be further configured to output information associated with the calculated air quality through at least one of the display or the wireless communication module.

The processor may be further configured to control the gas sensor to acquire the data associated with the air outside the electronic device, and to recognize the user gesture of starting the proximity call, based on at least data acquired from the proximity sensor when the electronic device is in communication with an external device via the wireless communication module.

According to an embodiment of the present disclosure, an electronic device may comprise a housing having a hole formed therein; a microphone located inside the housing and communicating with an outside of the electronic device through the hole; a gas sensor located inside the housing and communicating with the outside through the hole; a proximity sensor located inside the housing; a wireless communication module located inside the housing; and a processor located inside the housing and electrically connected to the microphone, the gas sensor, the proximity sensor, and the wireless communication module. The processor may be configured to recognize a user gesture of starting a proximity call, based on at least data acquired from the proximity sensor when the electronic device is in communication with an external device via the wireless communication module, and to measure a user's health status based on at least data acquired by the gas sensor after the user gesture of starting the proximity call is recognized.

The processor may be further configured to measure the user's health status, based on data acquired by the gas sensor after the user gesture of starting the proximity call is recognized and before a gesture of ending the proximity call is recognized.

According to various embodiments of the present disclosure, a method for operating an electronic device may comprise acquiring, by a gas sensor of the electronic device, data associated with air outside the electronic device; recognizing, by a processor of the electronic device, a user gesture of starting a proximity call, based on at least data acquired from a proximity sensor of the electronic device when the electronic device is in communication with an external device via a wireless communication module of the electronic device; and calculating, by the processor, air quality based on at least one of data acquired by the gas sensor before the proximity call starting gesture is recognized and data acquired by the gas sensor after a gesture of ending the proximity call is recognized.

According to an embodiment of the present disclosure, a method for operating an electronic device may comprise recognizing, by a processor of the electronic device, a user gesture of starting a proximity call, based on at least data acquired from a proximity sensor of the electronic device when the electronic device is in communication with an external device via a wireless communication module of the electronic device; and measuring, by the processor, a user's health status, based on at least data acquired by a gas sensor of the electronic device after the user gesture of starting the proximity call is recognized.

In this method, the processor may measure the user's health status, based on data acquired by the gas sensor after the user gesture of starting the proximity call is recognized and before the proximity call is ended.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the present disclosure has been particularly shown and described with reference to exemplary embodiments thereof, it is clearly understood that the same is by way of illustration and example only and is not to be taken in conjunction with the present disclosure. It will be understood by those skilled in the art that various changes in form and details may be made therein without departing from the subject matter and scope of the present disclosure.

What is claimed is:

1. An electronic device comprising:
a housing having a hole formed therein;
an audio device provided inside the housing and communicating with an outside of the electronic device through the hole;
a gas sensor provided inside the housing and communicating with the outside through the hole;
a proximity sensor provided inside the housing;
a wireless communication module provided inside the housing; and
a processor provided inside the housing and electrically connected to the audio device, the gas sensor, the proximity sensor, and the wireless communication module,
wherein the processor is configured to:
acquire data associated with air outside the electronic device by using the gas sensor,
recognize a user gesture of starting a proximity call by using the proximity sensor, and
calculate air quality based on at least one of data acquired by the gas sensor before the proximity call starting gesture is recognized and data acquired by the gas sensor after a gesture of ending the proximity call is recognized.

2. The electronic device of claim 1, wherein the audio device includes a microphone,
wherein the housing includes a first side facing a first direction, a second side facing a second direction opposite to the first direction, and a structure surrounding at least a portion of a space between the first side and the second side,
wherein the hole includes an outer opening formed in a front side of the structure, first and second inner openings formed in a rear side of the structure, and a passage extended from the outer opening to the first and second inner openings,
wherein the microphone is disposed on the rear side of the structure so as to allow air to flow into an opening of the microphone through the first inner opening, and
wherein the gas sensor is disposed on the rear side of the structure so as to allow air to flow into an opening of the gas sensor through the second inner opening.

3. The electronic device of claim 2, further comprising:
an attaching agent disposed around the first and second inner openings and configured to prevent a foreign matter from flowing into the space through the first and second inner openings.

4. The electronic device of claim 2, further comprising:
a first waterproof film attached to the opening of the microphone; and
a second waterproof film attached to the opening of the gas sensor.

5. The electronic device of claim 2, wherein the processor is further configured to drive the gas sensor when sound is acquired through the microphone.

6. The electronic device of claim 1, further comprising:
a display electrically connected to the processor,
wherein the processor is further configured to output information associated with the calculated air quality through at least one of the display or the wireless communication module.

7. The electronic device of claim 1, wherein the processor is further configured to drive the gas sensor during the proximity call.

8. The electronic device of claim 1, wherein the audio device includes a receiver,
wherein the housing includes a first side facing a first direction, a second side facing a second direction opposite to the first direction, and a structure surrounding at least a portion of a space between the first side and the second side,
wherein the hole includes an outer opening formed in a front side of the structure, first and second inner openings formed in a rear side of the structure, and a passage extended from the outer opening to the first and second inner openings,
wherein the receiver is disposed on the rear side of the structure so as to allow air to flow into an opening of the receiver through the first inner opening, and
wherein the gas sensor is disposed on the rear side of the structure so as to allow air to flow into an opening of the gas sensor through the second inner opening.

9. The electronic device of claim 8, further comprising:
an attaching agent disposed around the first and second inner openings and configured to prevent a foreign matter from flowing into the space through the first and second inner openings.

10. The electronic device of claim 8, further comprising:
a first waterproof film attached to the opening of the receiver; and
a second waterproof film attached to the opening of the gas sensor.

11. The electronic device of claim 8, wherein the processor is further configured to drive the gas sensor when the receiver is driven.

12. The electronic device of claim 11, wherein, when the receiver is not driven, the processor is further configured to control the receiver to output ultrasonic waves in response to occurrence of an event triggering an initiation of gas measurement using the gas sensor.

13. The electronic device of claim 11, wherein the processor is further configured to drive the gas sensor when position information acquired through the wireless communication module corresponds to a designated place.

14. The electronic device of claim 11, further comprising:
a display electrically connected to the processor,
wherein the processor is further configured to output information associated with the calculated air quality through at least one of the display or the wireless communication module.

15. The electronic device of claim 1, wherein the processor is further configured to control the gas sensor to acquire the data associated with the air outside the electronic device, and to recognize the user gesture of starting the proximity call, based on at least data acquired from the proximity sensor when the electronic device is in communication with an external device via the wireless communication module.

16. A method for operating an electronic device, the method comprising:
acquiring, by a gas sensor of the electronic device, data associated with air outside the electronic device;
recognizing, by a processor of the electronic device, a user gesture of starting a proximity call based on at least data acquired from a proximity sensor of the electronic device when the electronic device is in communication with an external device via a wireless communication module of the electronic device; and
calculating, by the processor, air quality based on at least one of data acquired by the gas sensor before the proximity call starting gesture is recognized and data acquired by the gas sensor after a gesture of ending the proximity call is recognized.

* * * * *